(12) United States Patent
Hu et al.

(10) Patent No.: US 11,774,287 B2
(45) Date of Patent: Oct. 3, 2023

(54) RAMAN SPECTROSCOPY INTEGRATED PERFUSION CELL CULTURE SYSTEM FOR MONITORING AND AUTO-CONTROLLING PERFUSION CELL CULTURE

(71) Applicant: Wuxi Biologics Ireland Limited, Dundalk (IE)

(72) Inventors: Jun Hu, Shanghai (CN); Gong Chen, Shanghai (CN); Yongjun Qin, Shanghai (CN); Weichang Zhou, Shanghai (CN)

(73) Assignee: WUXI BIOLOGICS IRELAND LIMITED, Dundalk (IE)

( * ) Notice: Subject to any disclaimer, the term of this patent is extended or adjusted under 35 U.S.C. 154(b) by 184 days.

(21) Appl. No.: 17/613,760

(22) PCT Filed: May 27, 2020

(86) PCT No.: PCT/CN2020/092441
§ 371 (c)(1),
(2) Date: Nov. 23, 2021

(87) PCT Pub. No.: WO2020/238918
PCT Pub. Date: Dec. 3, 2020

(65) Prior Publication Data
US 2022/0299370 A1  Sep. 22, 2022

(30) Foreign Application Priority Data

May 28, 2019 (WO) ................ PCT/CN2019/088722

(51) Int. Cl.
*G01J 3/44* (2006.01)
*C12M 1/00* (2006.01)
*G01N 21/65* (2006.01)

(52) U.S. Cl.
CPC ............... *G01J 3/44* (2013.01); *C12M 21/00* (2013.01); *C12M 29/10* (2013.01); *G01N 21/65* (2013.01)

(58) Field of Classification Search
CPC .......... G01J 3/44; G01N 21/64; G01N 21/65; C12M 21/00; C12M 29/10; C12M 41/46; C12M 41/48
See application file for complete search history.

(56) References Cited

U.S. PATENT DOCUMENTS

2009/0104594 A1  4/2009  Webb
2010/0075413 A1  3/2010  Zijlstra et al.
(Continued)

FOREIGN PATENT DOCUMENTS

CN  101416059 A  4/2009
CN  101443444 A  5/2009
(Continued)

OTHER PUBLICATIONS

International Search Report dated Aug. 26, 2020, for PCT Application No. PCT/CN2020/092441, filed on May 27, 2020, 4 pages.
(Continued)

*Primary Examiner* — Abdullahi Nur
(74) *Attorney, Agent, or Firm* — James S. Keddie; Bozicevic, Field & Francis LLP

(57) ABSTRACT

A Raman spectroscopy integrated perfusion cell culture system for monitoring and auto-controlling perfusion cell culture, comprising: a bioreactor, comprising: (1) an interior chamber for receiving a cell culture, (2) a port for feeding nutrient materials from a feed reservoir into the interior chamber, (3) a port for auto-bleeding from the interior chamber, and (4) a port for continuously harvesting materials from the interior chamber with the help of a cell retention system; a Raman analyzer, comprising (i) one or
(Continued)

more Raman probes which are immersed into the bioreactor and is configured to collect Raman spectrum in the bioreactor, and (ii) a host computer which is configured to receive the Raman spectrum collected and transferred by the Raman probe and turn it into values; and a controller in communication with the Raman analyzer, the feed reservoir and an auto-bleeding device, the controller being configured to receive the values from the Raman analyzer and compare them with preset parameters, based on results from comparing, the controller further being configured to control the feed reservoir for adjusting the feeding rate of nutrient materials into the bioreactor, and being configured to control the auto-bleeding device for auto-bleeding materials from the bioreactor. A process for monitoring and auto-controlling perfusion cell culture by using this system.

20 Claims, 8 Drawing Sheets

(56) References Cited

U.S. PATENT DOCUMENTS

| | | | |
|---|---|---|---|
| 2014/0295532 A1 | 10/2014 | Ray et al. | |
| 2015/0204763 A1 | 7/2015 | Stelzle et al. | |
| 2016/0025633 A1* | 1/2016 | Moretto | G01N 21/65 435/34 |
| 2017/0349874 A1 | 12/2017 | Jaques et al. | |
| 2018/0291329 A1 | 10/2018 | Moretto et al. | |
| 2019/0031997 A1 | 1/2019 | Hiller et al. | |
| 2019/0112569 A1 | 4/2019 | Czeterko et al. | |
| 2019/0137338 A1* | 5/2019 | Webster | C12N 5/0606 |
| 2019/0153381 A1 | 5/2019 | Angelini et al. | |

FOREIGN PATENT DOCUMENTS

| | | |
|---|---|---|
| CN | 104263700 A | 1/2015 |
| CN | 106834117 A | 6/2017 |
| CN | 107922919 A | 4/2018 |
| CN | 108884428 A | 11/2018 |
| CN | 109714962 A | 5/2019 |
| WO | WO 2005/010162 A2 | 2/2005 |
| WO | WO-2006/071716 A2 | 7/2006 |
| WO | WO-2016/196261 A1 | 12/2016 |
| WO | WO-2017/132185 A1 | 8/2017 |
| WO | WO 2017/207822 A1 | 12/2017 |
| WO | WO 2018/011805 A2 | 1/2018 |

OTHER PUBLICATIONS

Written Opinion of the International Searching Authority dated Aug. 26, 2020, for PCT Application No. PCT/CN2020/092441, filed on May 27, 2020, 4 pages.

Pully et al., "Microbioreactors for Raman Microscopy of Stromal Cell Differentiation", Anal. Chem., 2010, 82: 1844-1850.

* cited by examiner (a) IgG SNV-1D 800-1800

(b) Viability SNV-1D VIP>0.5

(c) Glutamine SNV-1D VIP>0.5

(d) Glutamate SNV-1D VIP>0.5

(e) Glucose SNV-2D 800-1800

(f) Lactate SNV-1D 600-1700 VIP>0.5

(g) $NH_4^+$ SNV-1D 800-1600

(h) Osmolality SNV-1D 800-1800

(i) $Na^+$ SNV-1D 800-3400

(j) $K^+$ SNV-2D all wavelength (k) $pCO_2$ SNV-1D VIP>0.5

(a) SNV-1D FC0A 1-50 days (b) SNV-2D FC0A 1-50 days (c) SNV-1D FC0B (d) SNV-2D FC0B (e) SNV-1D FC0A 1-50 days and FC0B (f) SNV-2D FC0A 1-50 days and FC0B (A) SNV-1D FC0A 1-50 days (B) SNV-2D FC0A 1-50 days (a) SNV-1D FC0A 1-50 days (b) SNV-2D FC0A 1-50 days (c) SNV-1D FC0B (d) SNV-2D FC0B (e) SNV-1D FC0A 1-50 days and FC0B (f) SNV-2D FC0A 1-50 days and FC0B

RAMAN SPECTROSCOPY INTEGRATED PERFUSION CELL CULTURE SYSTEM FOR MONITORING AND AUTO-CONTROLLING PERFUSION CELL CULTURE

INFORMATION OF PRIORITY

The present application is a U.S. National Phase application, filed under 35 U.S.C. § 371, of International Application No. PCT/CN2020/092441, filed on May 27, 2020, which claims priority to, and the benefit of, International Application No. PCT/CN2019/088722 filed on May 28, 2019, the entirety of the disclosure of each of which is incorporated herein by reference.

FIELD OF THE INVENTION

The present disclosure generally relates to a Raman spectroscopy integrated perfusion cell culture system for monitoring and auto-controlling perfusion cell culture. The present disclosure also relates to a process for monitoring and auto-controlling perfusion cell culture by using this system.

BACKGROUND OF THE INVENTION

Recently, the concept of Quality by Design (QBD) and Process Analytical Technology (PAT)[1][2] are widely accepted and applied to assist to evaluate the process robustness, monitor and improve process development and pharmaceutical manufacturing. PAT, especially in situ and real-time monitoring technology, shows promising potential in developing robust and novel process for producing the product with the desired quality attributes. It could also help to further understand the process by enabling a convenient, substantial and continuous measurements thereby augmenting conventional off-line analytics.

Spectroscopic methods such as near-infrared (NIR), mid-infrared (MIR), Raman and fluorescence spectroscopy were reported with advancements in bioprocess monitor and control[6][7]. Due to high chemical specificity, low interference from water and sample preparation, Raman spectroscopy technology was driving more and more attention in bio-pharmaceutical researching and manufacturing in the past decades. The utilization of immerse Raman probe can help to realize in-situ measurements and enable real-time process control as a promising PAT tool[8]. However, due to the complexity of perfusion devices and the challenge of sterility, in-situ and real time monitor PAT tools were hardly utilized during perfusion cell culture.

Perfusion cell culture[5], as a strategy for continuous process, is well established recently and attracted extensive attention for higher product yield and stable PQA (Product Quality Attributes). With ATF (Alternating Tangential Flow) devices, unexpected by-products like lactate, ammonium ions, dissolved carbon dioxide and some other byproducts, are removed while fresh nutrients are added continuously. With perfusion strategy, higher viable cell density (VCD) and higher productivity could be both archived just in a small-sized bioreactor[6][3]. Typically, perfusion processes perform at a certain target cell density by introducing a cell-bleeding system to maintain a relative steady state, meanwhile, the stability and quality of recombinant proteins are preserved due to the shorter product retention time.

In recent FDA's guidance on continuous manufacturing [4], product quality issues were addressed and emphasized, so the guidance recommend process monitoring and utilization of PAT tools to help generate real time information on process parameters and attributes of input materials, in-process materials, and final products for the duration of the manufacture, which could light the way for high detectability of transient disturbances, process deviation, active process control, more accurate material diversion and real time release testing (RTRT). Therefore, FDA expects that adopting continuous manufacturing for pharmaceutical production with enhanced development approach like QbD and PAT to reduce drug product quality issues, lower manufacturing costs and improve availability of quality medicines to patients. However, as discussed above, due to the complexity of perfusion devices and the challenge of sterility, in-situ and real time monitor PAT tools were hardly utilized during perfusion cell culture. Up to date, perfusion cell culture still mainly depends on traditional mankind sampling and off-line/at-line test for process monitoring, which leads to probable long delay after off-line sampling, making it difficult to have corrective actions if necessary and increasing the risk of batch loss. Moreover, manual operations introduce more risks of human error that might lead to contaminations. And thus, there is an urgent need for automatic PAT tools for perfusion cell culture, which can monitor and auto-control perfusion cell culture, thereby reducing manual operations, providing in situ and real time monitoring results for auto-control in lab scale and industrial scale.

SUMMARY OF THE INVENTION

This disclosure generally relates to a Raman spectroscopy integrated perfusion cell culture system for monitoring and auto-controlling perfusion cell culture. The present disclosure also relates to a process for monitoring and auto-controlling perfusion cell culture by using this system.

In some aspects, the present disclosure relates to a Raman spectroscopy integrated perfusion cell culture system for monitoring and auto-controlling perfusion cell culture, comprising:
  a bioreactor, comprising:
    (1) an interior chamber for receiving a cell culture,
    (2) a port for feeding nutrient materials from a feed reservoir into the interior chamber,
    (3) a port for auto-bleeding from the interior chamber, and
    (4) a port for continuously harvesting materials from the interior chamber with the help of a cell retention system;
  a Raman analyzer, comprising (i) one or more Raman probes which are immersed into the bioreactor and are configured to collect Raman spectrum in the bioreactor, and (ii) a host computer which is configured to receive the Raman spectrum collected and transferred by the Raman probe(s) and turn it into biochemical parameter values; and
  a controller in communication with the Raman analyzer, the feed reservoir and an auto-bleeding device, the controller being configured to receive the values from the Raman analyzer and compare them with preset parameters, and the controller further being configured to control the feed reservoir for adjusting the feeding rate of nutrient materials into the bioreactor, and being configured to control the auto-bleeding device for auto-bleeding materials from the bioreactor, based on results from comparing action.

In one embodiment, the bioreactor further comprises a rotatable shaft coupled to an agitator.

In one embodiment, in the Raman spectroscopy integrated perfusion cell culture system, the cell retention system is coupled to the bioreactor via the port for continuously harvesting materials from the interior chamber. The cell retention system includes, but not limited to, an Alternating Tangential Filtration (ATF) system, a Tangential Flow Filtration (TFF) system, an internal microfiltration system, a dielectrophoresis system, an acoustic resonance system and a gravitation, sedimentation system. One preferred cell retention system is ATF system. Typically, the ATF system includes a C24 controller, hollow fiber cartridge with polyethersulfone (PES) membrane, vacuum pump and customized tube. In use, the materials to be harvested are pumped into and out of the hollow fiber cartridge periodically, and the liquid contained in the materials is obtained from the pore in the hollow fiber continuously while cells contained in the materials are retained and pumped back into the bioreactor again by reverse flow.

In one embodiment, the Raman spectroscopy integrated perfusion cell culture system further comprises a product harvest reservoir. In one preferred embodiment, the product harvest reservoir is coupled to the cell retention system, and the cell retention system is coupled to the bioreactor.

In one embodiment, the Raman analyzer comprises more than one Raman probe, for example, 2, 3 or 4 Raman probes, especially immerse Raman probes. The Raman probes may measure different signals relative to each other.

In one embodiment, the Raman probes are configured to collect Raman spectrum in the bioreactor by detecting an intensity of scattered light in the bioreactor after the cell culture is exposed to a beam of light periodically.

In one embodiment, the Raman analyzer further comprises a laser-emitting module which emits a laser into the bioreactor with excitation wavelength of 785 nm periodically (e.g., 15 min~1 hour). At the same time, in order to avoid the influence of light from external portion of the bioreactor, the bioreactor is generally protected from external light during detection of Raman spectrum. For example, the bioreactor may be covered with a cover made of light-impermeable material. Therefore, in one embodiment, the Raman spectroscopy integrated perfusion cell culture system may further comprise a cover made of light-impermeable material, wherein the cover is configured to cover the bioreactor when the laser-emitting module of the Raman analyzer emits a laser into the bioreactor periodically and the Raman probes collect the Raman spectrum by detecting an intensity of scattered light in the bioreactor. In one embodiment, the bioreactor is light-impermeable per se, for example, made of light-impermeable material, and in such a situation, there is no need to protect the bioreactor from the external light during detection of Raman spectrum.

In one embodiment, the collected Raman spectrum is correlated to various standard reference measurements which have been performed off-line. For example, calibration spectra are first pre-processed by a Spectra Filter Module, and then correlated with the standard references via partial least square (PLS) regression.

In one embodiment, the collected Raman spectrum is correlated to biochemical indices, including, but not limited to, viable cell density (VCD), cell diameter, pH, $pCO_2$, $pO_2$, $Na^+$ ions and $K^+$ ions, glucose, glutamine, glutamate, lactate, ammonium ions and titer, osmolality and the like.

In one embodiment, the preset parameter values are input to the controller in advance. The controller is configured to receive the values of biochemical indices from the Raman analyzer and compare them with preset parameter values. In other words, the biochemical indices transferred from the Raman analyzer are compared with the preset parameter values in the controller. Based on the results of the comparing action, the controller controls the feed reservoir for adjusting the feeding rate of nutrient materials into the bioreactor, and controls the auto-bleeding device for auto-bleeding materials from the bioreactor, so as to maintain cell culture in a steady state.

In one embodiment, the materials auto-bled from the bioreactor is the same as those in the bioreactor at that moment, and generally comprise cells, products, metabolites, nutrients and some salts.

In one embodiment, the Raman spectroscopy integrated perfusion cell culture system is used to continuously incubate animal cells, plant cells, bacterial cells, or fungi cells, preferably animal cells, such as mammalian cells. The suitable mammalian cells include, but not limited to, Chinese hamster ovary (CHO) cells, for example CHO K1 cells, hybridomas, BHK (Baby Hamster Kidney) cells, myeloma cells, human cells, for example HEK-293 cells, human lymphoblastoid cells, E1 immortalized HER cells, mouse cells, for example NSO cells and SP/20 cells.

In one embodiment, the cells are incubated to produce products of interest, such as a monoclonal antibody, or a recombinant protein, and the like.

In some aspects, the present disclosure relates to a process for monitoring and auto-controlling perfusion cell culture by using the Raman spectroscopy integrated perfusion cell culture system, comprising:

(a) culturing a starting amount of cells in a starting volume of basal medium in a bioreactor, (b) collecting Raman spectrum by one or more Raman probes after exposing the cell culture to a beam of light periodically, and converting the collected Raman spectrum to biochemical indices by a host computer; and (c) adjusting feeding rate of nutrient materials from a feed reservoir into the bioreactor and auto-bleeding rate of materials from the bioreactor by a controller based on results from comparing the biochemical indices with corresponding preset parameter values input into the controller.

In one embodiment, the process of the present disclosure further comprises continuously harvesting a cell product of interest from the bioreactor with the help of a cell retention system.

In one embodiment, the process of the present disclosure further comprises maintaining cells in the bioreactor based on their sizes through a cell retention system. The cell retention system includes, but not limited to, an Alternating Tangential Filtration (ATF) system, a Tangential Flow Filtration (TFF) system, an internal microfiltration system, a dielectrophoresis system, an acoustic resonance system and a gravitation, sedimentation system. One preferred cell retention system is ATF system. Typically, the ATF system includes a C24 controller, hollow fiber cartridge with polyethersulfone (PES) membrane, vacuum pump and customized tube. In use, the materials to be harvested are pumped into and out of the hollow fiber cartridge periodically, and the liquid contained in the materials is obtained from the pore in the hollow fiber continuously while cells contained in the materials are retained and pumped back into the bioreactor again by reverse flow.

In one embodiment, the Raman spectrum is collected through Raman probes by detecting an intensity of scattered light in the bioreactor when a laser-emitting module emits a laser into the bioreactor with excitation wavelength of 785 nm periodically (e.g., 15 min 1 hour). In one embodiment, the bioreactor is generally protected from external light during detection of Raman spectrum, so as to avoid the influence of light from external portion of the bioreactor. For example, the bioreactor may be covered with a cover made of light-impermeable material. In one embodiment, the bioreactor is light-impermeable per se, for example, made of light-impermeable material, and in such a situation, there is no need to protect the bioreactor from the external light during detection of Raman spectrum.

In one embodiment, the collected Raman spectrum is correlated to various standard reference measurements which have been performed off-line. For example, calibration spectra are first pre-processed by a Spectra Filter Module, and then correlated with the standard references via partial least square (PLS) regression.

In one embodiment, the collected Raman spectrum is correlated to biochemical indices, including, but not limited to, viable cell density (VCD), cell diameter, pH, $pCO_2$, $pO_2$, $Na^+$ ions and $K^+$ ions, glucose, glutamine, glutamate, lactate, ammonium ions and titer, osmolality and the like.

In one embodiment, the preset parameter values are input to the controller in advance. The biochemical indices transferred from the Raman analyzer are compared with the preset parameter values in the controller. Based on the results of the comparing action, the controller controls the feed reservoir for adjusting the feeding rate of nutrient materials into the bioreactor, and controls the auto-bleeding device for auto-bleeding materials from the bioreactor, so as to maintain cell culture in a steady state.

In one embodiment, the process is used to continuously incubate animal cells, plant cells, bacterial cells, or fungi cells, preferably animal cells, such as mammalian cells. The suitable mammalian cells include, but not limited to, Chinese hamster ovary (CHO) cells, for example CHO K1 cells, hybridomas, BHK (Baby Hamster Kidney) cells, myeloma cells, human cells, for example HEK-293 cells, human lymphoblastoid cells, E1 immortalized HER cells, mouse cells, for example NS0 cells and SP/20 cells.

In one embodiment, the cells are incubated to produce products of interest, such as a monoclonal antibody, or a recombinant protein, and the like.

The foregoing is a summary and thus contains, by necessity, simplifications, generalizations, and omissions of detail; consequently, those skilled in the art will appreciate that the summary is illustrative only and is not intended to be in any way limiting. Other aspects, features, and advantages of the methods, compositions and/or devices and/or other subject matter described herein will become apparent in the teachings set forth herein. The summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter. Further, the contents of all references, patents and published patent applications cited throughout this application are incorporated herein in entirety by reference.

DETAILED DESCRIPTION OF THE INVENTION

Figure 1:
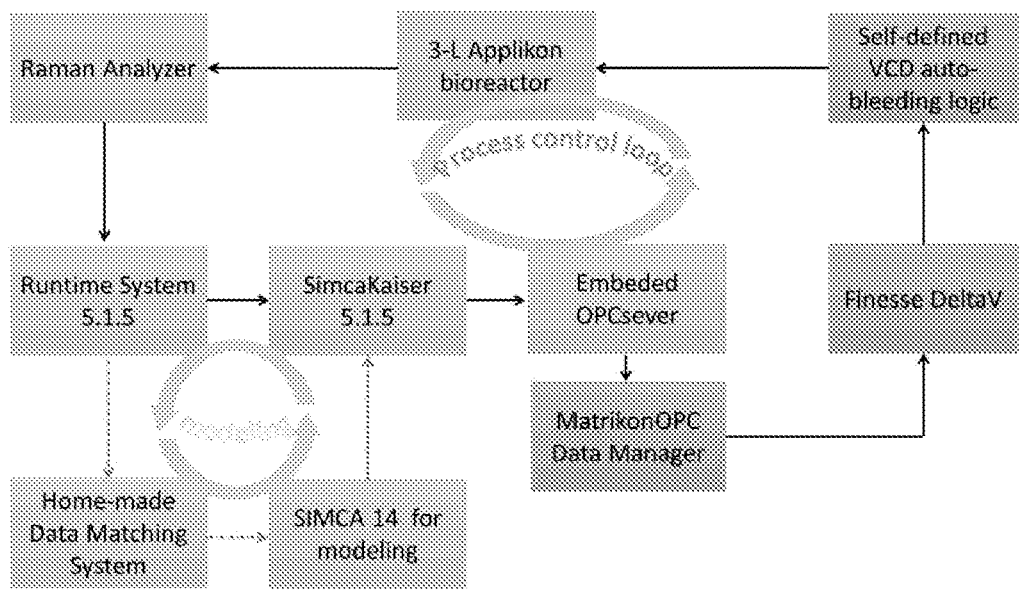
FIG. 1 is a schematic diagram of hardware, software, networking, and communication infrastructure utilized for VCD feedback control capability.

While the present invention may be embodied in many different forms, disclosed herein are specific illustrative embodiments thereof that exemplify the principles of the invention. It should be emphasized that the present invention is not limited to the specific embodiments illustrated. Moreover, any section headings used herein are for organizational purposes only and are not to be construed as limiting the subject matter described.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. More specifically, as used in this specification and the appended claims, the singular forms "a," "an" and "the" include plural referents unless the context clearly dictates otherwise. Thus, for example, reference to "a protein" includes a plurality of proteins; reference to "a cell" includes mixtures of cells, and the like. In this application, the use of "or" means "and/or" unless stated otherwise. Furthermore, the use of the term "comprising," as well as other forms, such as "comprises" and "comprised," is not limiting. In addition, ranges provided in the specification and appended claims include both end points and all points between the end points.

Generally, nomenclature used in connection with, and techniques of, cell and tissue culture, molecular biology, immunology, microbiology, genetics and protein and nucleic acid chemistry and hybridization described herein are those well-known and commonly used in the art. The methods and techniques of the present invention are generally performed according to conventional methods well known in the art and as described in various general and more specific references that are cited and discussed throughout the present specification unless otherwise indicated. The nomenclature used in connection with, and the laboratory procedures and techniques of, analytical chemistry, synthetic organic chemistry, and medicinal and pharmaceutical chemistry described herein are those well-known and commonly used in the art. Moreover, any section headings used herein are for organizational purposes only and are not to be construed as limiting the subject matter described.

Definitions

In order to better understand the invention, the definitions and explanations of the relevant terms are provided as follows.

The term "perfusion cell culture" refers to a continuous process of incubating cells. Perfusion is upstream processing which retains cells inside the bioreactor while continually removing cells, cell waste products and media depleted of nutrients by cell metabolism. Fresh media is provided to the cells at the same rate as the spent media is removed. The most common means to achieve perfusion is the use of hollow fiber filtration in the mode of ATF. With aid of ATF devices, unexpected by-products like lactate, ammonium, dissolved carbon dioxide and some other byproducts, are removed while fresh nutrients are added continuously.

A "bioreactor" as defined herein is a device that comprises cell culture (i.e., cells and a medium for culture). It preferably maintains a favorable environment for the cells by providing appropriate conditions such as temperature, pH, dissolved oxygen concentration, ions concentration, continuous stirring, and the like. It preferably provides sterile environment.

In general, the bioreactor, for instance, may comprise a fermenter, a stirred-tank reactor, an adherent bioreactor, a wave-type bioreactor, a disposable bioreactor, and the like.

Raman spectroscopy measures changes in the vibrational frequency of component specific molecular bonds. Raman provides complimentary information to more traditional mid-1 R spectroscopy, while having more utility in aqueous solutions due to its resistance to water interference, making it desirable for bioreactor applications.

Raman spectra collected from inline Raman probes, coupled with a host computer capable of multivariate analysis (MVA), can be used to monitor metabolites and cell concentration within the bioreactor. Raman spectroscopy provides the ability to monitor bioprocesses in real time which allows for the implementation of feedback controls for nutrient feeds leading to improved product quality and cell productivity.

A "Raman analyzer" as used herein refer to a device capable of collecting Raman spectrum in the bioreactor through one or more Raman probes and converting the collected Raman spectrum to biochemical parameter values, such as viable cell density (VCD), cell diameter, pH, $pCO_2$, $pO_2$, $Na^+$ ions and $K^+$ ions, glucose, glutamine, glutamate, lactate, ammonium ions and titer, osmolality and the like.

The Raman analyzer generally comprises (i) one or more Raman probes which are immersed into the bioreactor and are configured to collect Raman spectrum in the bioreactor, and (ii) a host computer which is configured to receive the Raman spectrum collected and transferred by the Raman probe and turn it into biochemical parameter values. The Raman analyzer further comprises (iii) a laser-emitting module, which emits a laser into the bioreactor with excitation wavelength of 785 nm periodically (e.g., 15 min~1 hour).

A "controller" as used herein refers to a controlling device coupled with the Raman analyzer and in communication with a feed reservoir and an auto-bleeding device. The controller receives the converted biochemical parameter values transferred from the Raman analyzer and compares them with corresponding preset parameter values input to the controller in advance. Based on results from the comparing action, the controller automatically adjusts the feeding rate of nutrient materials from the feed reservoir into the bioreactor and auto-bleeding rate of materials from the bioreactor.

Figure 2:
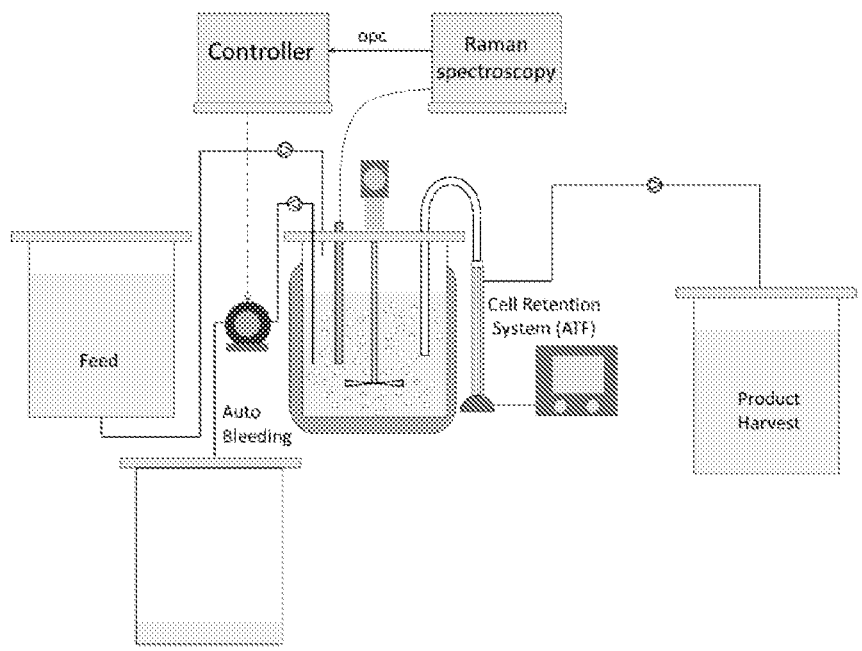
FIG. 2 is a schematic diagram of a Raman spectroscopy integrated perfusion cell culture system for monitoring and auto-controlling perfusion cell culture according to one embodiment of the present disclosure.

"Auto-bleeding" as used herein refers to a Raman-perfusion cell culture integrated auto-process control loop which is capable of controlling the viable cell density in the bioreactor within the deadband of target via bleeding system shown in FIG. 2 automatically.

"Cell retention system" as used herein refers to a cell retention device, i.e. cross-flow membrane filters, like an ATF system, through which the product harvest is obtained while the cells are kept in the bioreactor based on their sizes. A Raman Spectroscopy Integrated Perfusion Cell Culture System for Monitoring and Auto-Controlling Perfusion Cell Culture The Raman spectroscopy integrated perfusion cell culture system for monitoring and auto-controlling perfusion cell culture comprises:
 a bioreactor, comprising:
  (1) an interior chamber for receiving a cell culture,
  (2) a port for feeding nutrient materials from a feed reservoir into the interior chamber,
  (3) a port for auto-bleeding from the interior chamber, and
  (4) a port for continuously harvesting materials from the interior chamber with the help of a cell retention system;
 a Raman analyzer, comprising (i) one or more Raman probes which are immersed into the bioreactor and are configured to collect Raman spectrum in the bioreactor, and (ii) a host computer which is configured to receive the Raman spectrum collected and transferred by the Raman probe(s) and turn it into biochemical parameter values; and
 a controller in communication with the Raman analyzer, the feed reservoir and an auto-bleeding device, the controller being configured to receive the values from the Raman analyzer and compare them with preset parameters, and the controller further being configured to control the feed reservoir for adjusting the feeding rate of nutrient materials into the bioreactor, and being configured to control the auto-bleeding device for auto-bleeding materials from the bioreactor, based on results from comparing action.

In one embodiment, the bioreactor further comprises a rotatable shaft coupled to an agitator.

There are no specific limitations to the bioreactor. Those skilled in the art can select suitable bioreactor in accordance with practical requirements. The bioreactor, for instance, may comprise a fermenter, a stirred-tank reactor, an adherent bioreactor, a wave-type bioreactor, a disposable bioreactor, and the like.

The bioreactor can have any suitable volume. For instance, the volume of the bioreactor can be from 0.1 mL to about 25,000 L or larger. For example, the volume of the bioreactor can be greater than about 0.5 L, such as greater than about 1 L, such as greater than about 2 L, such as greater than about 3 L, such as greater than about 4 L, such as greater than about 5 L, such as greater than about 6 L, such as greater than about 7 L, such as greater than about 8 L, such as greater than about 10 L, such as greater than about 12 L, such as greater than about 15 L, such as greater than about 20 L, such as greater than about 25 L, such as greater than about 30 L, such as greater than about 35 L, such as greater than about 40 L, such as greater than about 45 L. The volume of the bioreactor is generally less than about 25,000 L, such as less than about 15,000 L, such as less than about 10,000 L, such as less than about 5,000 L, such as less than about 1,000 L, such as less than about 800 L, such as less than about 600 L, such as less than about 400 L, such as less than about 200 L, such as less than about 100 L, such as less than about 50 L, such as less than about 40 L, such as less than about 30 L, such as less than about 20 L, such as less than about 10 L. In one embodiment, for instance, the volume of the bioreactor can be from about 1 L to about 5 L. In an alternative embodiment, the volume of the bioreactor can be from about 25 L to about 75 L. In still another embodiment, the volume of the bioreactor can be from about 1,000 L to about 5,000 L.

In one embodiment, in the Raman spectroscopy integrated perfusion cell culture system, the cell retention system is coupled to the bioreactor via the port for continuously harvesting materials from the interior chamber.

In one embodiment, the cell retention system is composed of cross-flow membrane filters, like an ATF system. There are many cell retention systems which can be selected by those skilled in the art, provided that the product harvest is obtained while the cells are kept in the bioreactor based on their sizes through the cell retention system. For example, the cell retention system includes, but not limited to, an ATF (Alternating Tangential Filtration) system, a Tangential Flow Filtration (TFF) system, an internal microfiltration system, a dielectrophoresis system, an acoustic resonance system and a gravitation, sedimentation system. One preferred cell retention system is ATF system. Typically, the ATF system includes a C24 controller, hollow fiber cartridge with polyethersulfone (PES) membrane, vacuum pump and customized tube. In use, the materials to be harvested are pumped into and out of the hollow fiber cartridge periodically, and the liquid contained in the materials is obtained from the pore in the hollow fiber continuously while cells contained in the materials are retained and pumped back into the bioreactor again by reverse flow.

In one embodiment, the Raman spectroscopy integrated perfusion cell culture system further comprises a product harvest reservoir. In one preferred embodiment, the product harvest reservoir is coupled to the cell retention system, and the cell retention system is coupled to the bioreactor.

In one embodiment, the Raman analyzer comprises more than one Raman probe, for example, 2, 3 or 4 Raman probes, especially immerse Raman probes. The Raman probes may measure different signals relative to each other.

In one embodiment, the Raman probes are configured to collect Raman spectrum in the bioreactor by detecting an intensity of scattered light in the bioreactor after the cell culture is exposed to a beam of light periodically.

In one embodiment, the Raman analyzer further comprises a laser-emitting module which emits a laser into the bioreactor with excitation wavelength of 785 nm periodically (e.g., 15 min~1 hour). At the same time, in order to avoid the influence of light from external portion of the bioreactor, the bioreactor is generally protected from external light during detection of Raman spectrum. For example, the bioreactor may be covered with a cover made of light-impermeable material. Therefore, in one embodiment, the Raman spectroscopy integrated perfusion cell culture system may further comprise a cover made of light-impermeable material, wherein the cover is configured to cover the bioreactor when the laser-emitting module of the Raman analyzer emits a laser into the bioreactor periodically and the Raman probes collect the Raman spectrum by detecting an intensity of scattered light in the bioreactor. In one embodiment, the bioreactor is light-impermeable per se, for example, made of light-impermeable material, and in such a situation, there is no need to protect the bioreactor from the external light during detection of Raman spectrum.

In one embodiment, the collected Raman spectrum is correlated to various standard reference measurements which have been performed off-line. For example, calibration spectra are first pre-processed by a Spectra Filter Module, and then correlated with the standard references via partial least square (PLS) regression.

In one embodiment, the collected Raman spectrum is correlated to biochemical indices, including, but not limited to, viable cell density (VCD), cell diameter, pH, $pCO_2$, $pO_2$, $Na^+$ ions and $K^+$ ions, glucose, glutamine, glutamate, lactate, ammonium ions and titer, osmolality and the like.

The pH, dissolved oxygen concentration and osmolality of the cell culture medium are in principle not critical and depend on the type of cell chosen. Preferably, the pH, dissolved oxygen concentration and osmolality are chosen such that it is optimal for the growth and productivity of the cells. The person skilled in the art knows how to determine the optimal pH, dissolved oxygen concentration and osmolality for the culture (see e.g. WO 2004/099396). Preferably, for the system of the present disclosure the pH is chosen between 6.6 and 7.6 and/or the osmolality is chosen between 260 and 400 mOsm/kg. The temperature inside the bioreactor is from 20° C. to 40° C., preferably from 30° C. to 40° C., more preferably 31.0 to 37.0° C. To maintain optimal process conditions, automation to control the process conditions is achieved by using the Raman spectroscopy integrated perfusion cell culture system.

In one embodiment, the preset parameter values are input to the controller in advance. The controller is configured to receive the values of biochemical indices from the Raman analyzer and compare them with preset parameter values. In other words, the biochemical indices transferred from the Raman analyzer are compared with the preset parameter values in the controller. Based on the results of the comparing action, the controller controls the feed reservoir for adjusting the feeding rate of nutrient materials into the bioreactor, and controls the auto-bleeding device for auto-bleeding materials from the bioreactor, so as to maintain cell culture in a steady state.

In one embodiment, the materials auto-bled from the bioreactor are the same as those in the bioreactor at that moment, and generally comprise cells, products, metabolites, nutrients and some salts.

In one embodiment, the Raman spectroscopy integrated perfusion cell culture system is used to continuously incubate animal cells, plant cells, bacterial cells, or fungi cells, preferably animal cells, such as mammalian cells. The suitable mammalian cells include, but not limited to, Chinese hamster ovary (CHO) cells, for example CHO K1 cells, hybridomas, BHK (Baby Hamster Kidney) cells, myeloma cells, human cells, for example HEK-293 cells, human lymphoblastoid cells, E1 immortalized HER cells, mouse cells, for example NSO cells and SP/20 cells.

In one embodiment, the cells are incubated to produce products of interest, such as a monoclonal antibody, or a recombinant protein, and the like.

For instance, cells that produce a product of interest are cells capable of expressing a gene encoding the cell product. Cells capable of expressing a gene encoding the cell product may for example be prepared by transfection of the cells with a plasmid containing the gene encoding the cell product and gene encoding a suitable selection marker.

Products of interest, which may be produced by the cells, for example by expressing a (recombinant) gene coding the same are for example (recombinant) proteins, in particular receptors, enzymes, fusion proteins, blood proteins such as proteins from the blood coagulation cascade, multifunctional proteins such as for instance erythropoietin, virus or bacterial proteins for instance for use in vaccines; immunoglobulins such as antibodies, for example IgG or IgM, and the like. Preferably a protein, more preferably an antibody is produced by the cells. Preferably, the cell products such as proteins or vaccines produced by the cells can be used as an active ingredient in a pharmaceutical preparation. Cell products, which may be produced by the cells, for example by expressing a (recombinant) gene coding therefore are for example (recombinant) proteins, in particular receptors, enzymes, fusion proteins, blood proteins such as proteins from the blood coagulation cascade, multifunctional proteins such as for instance erythropoietin, virus or bacterial proteins for instance for use in vaccines; immunoglobulins such as antibodies, for example IgG or IgM, and the like. Preferably a protein, more preferably an antibody is produced by the cells. Preferably, the cell products such as proteins or vaccines produced by the cells can be used as an active ingredient in a pharmaceutical preparation. Cell products, which may be produced by the cells, for example by expressing a (recombinant) gene coding therefore are for example (recombinant) proteins, in particular receptors, enzymes, fusion proteins, blood proteins such as proteins from the blood coagulation cascade, multifunctional proteins such as for instance erythropoietin, virus or bacterial proteins for instance for use in vaccines; immunoglobulins such as antibodies, for example IgG or IgM, and the like. Preferably a protein, more preferably an antibody is produced by the cells. Preferably, the cell products such as proteins or vaccines produced by the cells can be used as an active ingredient in a pharmaceutical composition.

In a specific embodiment, the products of interest are products useful in a pharmaceutical composition. They can be used as a medicine, in particular as a medicine in humans. Such a medicine may for example be used for diagnosis, or for prophylactic purpose such as for instance a vaccine, and/or for therapeutic purpose, such as for instance an enzyme or protein for which a patient is deficient, or an antibody to kill undesired cells. In addition to the products of interest produced by the perfusion cell culture of the present application, a pharmaceutical composition may further contain a pharmaceutically acceptable carrier or excipient, examples of which are well known to the person skilled in the art.

Examples of proteins that can be used as an active ingredient in pharmaceutical preparations (with the brand name between brackets) include, but are not limited to, Tenecteplase (TN Kase™), (recombinant) antihemophilic factor (ReFacto™) lymphoblastoid Interferon α-n1 (Wellferon™), (recombinant) Coagulation factor (NovoSeven™), Etanercept, (Enbrel™), Trastuzumab (Herceptin™), Infliximab (Remicade™), Palivizumab (Synagis™), Basiliximab (Simulect™), Daclizumab (Zenapaz™), Rituximab (Rituxan™), (recombinant) Coagulation factor IX (Benefix™) and Interferon β-1a (Avonex™).

Examples of vaccines that can be used as an active ingredient in pharmaceutical preparation include isolated protein antigens, examples of which include but are not limited to live, oral, tetravalent Rotavirus vaccine (RotaShield™), rabies vaccine (RanAvert™), influenza vaccines and inactivated hepatitis A vaccine (VAQTA™).

A Process for Monitoring and Auto-Controlling Perfusion Cell Culture by Using Raman Spectroscopy Integrated Perfusion Cell Culture System The process for monitoring and auto-controlling perfusion cell culture by using the Raman spectroscopy integrated perfusion cell culture system comprises:

(a) culturing a starting amount of cells in a starting volume of basal medium in a bioreactor, (b) collecting Raman spectrum by one or more Raman probes after exposing the cell culture to a beam of light periodically, and converting the collected Raman spectrum to biochemical indices by a host computer; and (c) adjusting feeding rate of nutrient materials from a feed reservoir into the bioreactor and auto-bleeding rate of materials from the bioreactor by a controller based on results from comparing the biochemical indices with corresponding preset parameter values input into the controller.

In one embodiment, the process of the present disclosure further comprises continuously harvesting a cell product of interest from the bioreactor with the help of a cell retention system.

In one embodiment, the process of the present disclosure further comprises maintaining cells in the bioreactor based on their sizes through a cell retention system. The cell retention system includes, but not limited to, an Alternating Tangential Filtration (ATF) system, a Tangential Flow Filtration (TFF) system, an internal microfiltration system, a dielectrophoresis system, an acoustic resonance system and a gravitation, sedimentation system. One preferred cell retention system is ATF system. Typically, the ATF system includes a C24 controller, hollow fiber cartridge with polyethersulfone (PES) membrane, vacuum pump and customized tube. In use, the materials to be harvested are pumped into and out of the hollow fiber cartridge periodically, and the liquid contained in the materials is obtained from the pore in the hollow fiber continuously while cells contained in the materials are retained and pumped back into the bioreactor again by reverse flow.

In one embodiment, the Raman spectrum is collected through Raman probes by detecting an intensity of scattered light in the bioreactor when a laser-emitting module emits a laser into the bioreactor with excitation wavelength of 785 nm periodically (e.g., 15 min 1 hour). In one embodiment, the bioreactor is generally protected from external light during detection of Raman spectrum, so as to avoid the influence of light from external portion of the bioreactor. For example, the bioreactor may be covered with a cover made of light-impermeable material. In one embodiment, the bioreactor is light-impermeable per se, for example, made of light-impermeable material, and in such a situation, there is no need to protect the bioreactor from the external light during detection of Raman spectrum.

In one embodiment, the collected Raman spectrum is correlated to various standard reference measurements which have been performed off-line. For example, calibration spectra are first pre-processed by a Spectra Filter Module, and then correlated with the standard references via partial least square (PLS) regression.

In one embodiment, the collected Raman spectrum is correlated to biochemical indices, including, but not limited to, viable cell density (VCD), cell diameter, pH, $pCO_2$, $pO_2$, $Na^+$ ions and $K^+$ ions, glucose, glutamine, glutamate, lactate, ammonium ions and titer, osmolality and the like.

The pH, dissolved oxygen concentration and osmolality of the cell culture medium are in principle not critical and depend on the type of cell chosen. Preferably, the pH, dissolved oxygen concentration and osmolality are chosen such that it is optimal for the growth and productivity of the cells. The person skilled in the art knows how to find the optimal pH, dissolved oxygen concentration and osmolality for the culture (see e.g. WO 2004/099396). Preferably, for the process of the present disclosure the pH is chosen between 6.6 and 7.6 and/or the osmolality is chosen between 260 and 400 mOsm/kg. The temperature inside the bioreactor is from 20° C. to 40° C., preferably from 30° C. to 40° C., more preferably from 31.0 to 37.0° C. To maintain optimal process conditions automation to control the process conditions is achieved by using the Raman spectroscopy integrated perfusion cell culture system.

In one embodiment, the preset parameter values are input to the controller in advance. The biochemical indices transferred from the Raman analyzer are compared with the preset parameter values in the controller. Based on the results of the comparing action, the controller controls the feed reservoir for adjusting the feeding rate of nutrient materials into the bioreactor, and controls the auto-bleeding device for auto-bleeding materials from the bioreactor, so as to maintain cell culture in a steady state.

There are no limitations to the preset parameter values, which are dependent on the cell type and the product produced by the cells. Those skilled in the art can determine suitable preset parameter values in accordance with the practical requirements.

In one embodiment, the process is used to continuously incubate animal cells, plant cells, bacterial cells, or fungi cells, preferably animal cells, such as mammalian cells. The suitable mammalian cells include, but not limited to, Chinese hamster ovary (CHO) cells, for example CHO K1 cells, hybridomas, BHK (Baby Hamster Kidney) cells, myeloma cells, human cells, for example HEK-293 cells, human lymphoblastoid cells, E1 immortalized HER cells, mouse cells, for example NSO cells and SP/20 cells.

In one embodiment, the cells are incubated to produce products of interest, such as a monoclonal antibody, or a recombinant protein, and the like.

For instance, cells that produce a product of interest are cells capable of expressing a gene encoding the cell product. Cells capable of expressing a gene encoding the cell product may for example be prepared by transfection of the cells with a plasmid containing the gene encoding the cell product and gene encoding a suitable selection marker.

Products of interest, which may be produced by the cells, for example by expressing a (recombinant) gene coding the same are for example (recombinant) proteins, in particular receptors, enzymes, fusion proteins, blood proteins such as proteins from the blood coagulation cascade, multifunctional proteins such as for instance erythropoietin, virus or bacterial proteins for instance for use in vaccines; immunoglobulins such as antibodies, for example IgG or IgM, and the like. Preferably a protein, more preferably an antibody is produced by the cells. Preferably, the cell products such as proteins or vaccines produced by the cells can be used as an active ingredient in a pharmaceutical preparation. Cell products, which may be produced by the cells, for example by expressing a (recombinant) gene coding therefore are for example (recombinant) proteins, in particular receptors, enzymes, fusion proteins, blood proteins such as proteins from the blood coagulation cascade, multifunctional proteins such as for instance erythropoietin, virus or bacterial proteins for instance for use in vaccines; immunoglobulins such as antibodies, for example IgG or IgM, and the like. Preferably a protein, more preferably an antibody is produced by the cells. Preferably, the cell products such as proteins or vaccines produced by the cells can be used as an active ingredient in a pharmaceutical preparation. Cell products, which may be produced by the cells, for example by expressing a (recombinant) gene coding therefore are for example (recombinant) proteins, in particular receptors, enzymes, fusion proteins, blood proteins such as proteins from the blood coagulation cascade, multifunctional proteins such as for instance erythropoietin, virus or bacterial proteins for instance for use in vaccines; immunoglobulins such as antibodies, for example IgG or IgM, and the like. Preferably a protein, more preferably an antibody is produced by the cells. Preferably, the cell products such as proteins or vaccines produced by the cells can be used as an active ingredient in a pharmaceutical composition.

In a specific embodiment, the products of interest are products useful in a pharmaceutical composition. They can be used as a medicine, in particular as a medicine in humans. Such a medicine may for example be used for diagnosis, or for prophylactic purpose such as for instance a vaccine, and/or for therapeutic purpose, such as for instance an enzyme or protein for which a patient is deficient, or an antibody to kill undesired cells. In addition to the products of interest produced by the perfusion cell culture of the present application, a pharmaceutical composition may further contain a pharmaceutically acceptable carrier or excipient, examples of which are well known to the person skilled in the art.

Examples of proteins that can be used as an active ingredient in pharmaceutical preparations (with the brand name between brackets) include, but are not limited to, Tenecteplase (TN Kase™), (recombinant) antihemophilic factor (ReFacto™) lymphoblastoid Interferon α-n1 (Wellferon™), (recombinant) Coagulation factor (NovoSeven™), Etanercept, (Enbrel™), Trastuzumab (Herceptin™), Infliximab (Remicade™), Palivizumab (Synagis™), Basiliximab (Simulect™), Daclizumab (Zenapaz™), Rituximab (Rituxan™), (recombinant) Coagulation factor IX (Benefix™) and Interferon β-1a (Avonex™).

Examples of vaccines that can be used as an active ingredient in pharmaceutical preparation include isolated protein antigens, examples of which include but are not limited to live, oral, tetravalent Rotavirus vaccine (RotaShield™), rabies vaccine (RanAvert™) influenza vaccines and inactivated hepatitis A vaccine (VAQTA™).

The process of the present disclosure can in principle be performed in any type of cell culture medium suitable for the culturing of cells. Guidelines for choosing a cell culture medium and cell culture conditions are well known and are for instance provided in Chapter 8 and 9 of Freshney, R. I. Culture of animal cells (a manual of basic techniques), 4th edition 2000, Wiley-Liss and in Doyle, A., Griffiths, J. B., Newell, D. G. Cell & Tissue culture: Laboratory Procedures 1993, John Wiley & Sons.

In preferred embodiments, the cell product produced in the process of the present disclosure is harvested from the cell culture that is removed from the bioreactor. The cell product(s) produced in the process of the present disclosure can be further harvested from the cell culture in so-called downstream processing, using methods dependent on the cell product, which methods are as such well known to the skilled person. Downstream processing usually comprises several purification steps in varying combinations and order. Examples of purification steps in the downstream processing are separation steps (e.g. by affinity chromatography and/or ion exchange chromatography and/or extraction by aqueous two-phase systems and/or precipitation by for example ammonium sulphate), steps for the concentration of the cell product (e.g. by ultrafiltration or diafiltration), steps to exchange buffers and/or steps to remove or inactivate viruses (e.g. by virus filtration, pH shift or solvent detergent treatment).

The rate of addition of at least one cell culture medium component, for example nutrients and/or cell culture medium to the cell culture (i.e., perfusion rate) influences the viability and the density of the cells. In the process of the present disclosure, the cell culture medium component(s), such as nutrients and/or cell culture medium may be fed for example in a continuous flow, semi-continuous flow, for example step-wise flow or staggered flow. Preferably, cell culture medium component(s), for example nutrients and/or cell culture medium are added in a continuous flow.

Technical Effect of the Present Disclosure

This present disclosure focuses on integration of Raman spectroscopy with perfusion cell culture. As shown in FIG. 2, the diagram showed how auto-bleeding is implemented in the Raman spectroscopy integrated perfusion cell culture system.

Perfusion was archived as feed medium was continuously fed into the bioreactor, and the cell product was continuously harvested with the help of cell retention system. Before the automatic control of VCD, cells were bled out of the bioreactor at a constant pumping rate which needs to be modified periodically. While Raman spectroscopy could detect the scattered laser intensity in the bioreactor and transfer the signal into multivariate values, those predicted biochemical indices were then delivered to the deltaV controller through OPC connection. In the deltaV controller, the difference between the real-time VCD and VCD set-point was put into the P.I.D (proportional-integral-derivative) algorithms, then the output, i.e. controller output went through the configuration setting, scaled to the suitable actuator output, eventually a pump was cascaded to the actuator output. Namely, the power of the pump was set to be proportional to the difference between the predicted VCD and target VCD. Besides, a high limit for pump power was set to ensure the system safety. P.I.D. strategy was also utilized to smooth and stabilize the on-line control of VCD.

EXAMPLES

The present invention, thus generally described, will be understood more readily by reference to the following Examples, which are provided by way of illustration and are not intended to be limiting of the instant invention. The Examples are not intended to represent that the experiments below are all or the only experiments performed.

Materials

Bioprocess controller system: Finesse G3Lab universal controller, TruBio Delta V 5.0 control software, 3 L Applikon glass bioreactor; 200 L XDR bioreactor (Xcellerex XDR-200).

ATF system: Repligen Alternating Tangential Flow (ATF2) system for 3 L bench-top bioreactor in which the hollow fiber module composed of polyethersulfone (PES) with pore size of 0.22 µm, 1 mm inner diameter (ID) and 0.047 $m^2$ filter size, as for ATF6 which was utilized for 200 L XDR bioreactor, the filter size was 2.5 $m^2$.

Raman system: Kaiser RAMANRXN2 Multi-channel Raman Analyzer (Kaiser Optical Systems, Inc., Ann Arbor, MI) with a laser excitation wavelength of 785 nm and up to four bIO-LAB-220 probes; Umetrics' SIMCA software version 14.1.2 (Umetrics Inc., San Jose, CA).

OPC connection system: embedded OPC server in Raman RunTime, MatrikonOPC data manage software (MatrikonOPC, Edmonton, Alberta, Canada).

Cell line and media: Chinese hamster ovary (CHO) cell line expressing human IgG1 monoclonal antibody, proprietary chemically defined basal and feed media which are commercially available.

Example 1

1. Cell Culture

An IgG1 monoclonal antibody producing Chinese hamster ovary (CHO) cell line was cultivated in perfusion mode in a 3 L bench top bioreactor with a constant working volume of 1500 mL. Proprietary chemically defined basal and feed media were used, which are commercially available. Bioreactors (3-L Applikon glass bioreactors, Applikon Biotechnology, The Netherlands) were operated at 34.5° C. The pH was controlled at 6.9±0.2 by addition of $CO_2$ gas to decrease pH and addition of 1 M $Na_2CO_3$ solution to increase pH if needed. The DO (Dissolved Oxygen) was maintained at 40% of air saturation through L-sparger and Microsparger (hole diameter of 1 mm and 100 µm, respectively). The set-point of agitation was 250 RPM.

The bioreactor was seeded at approximately $0.5 \times 10^6$ cells/mL. Basal medium perfusion was started on day 2 when VCD reached about $2.0 \times 10^6$ cells/mL. Cell bleeding was started when VCD reached more than $50 \times 10^6$ cells/mL. Cells have been cultivated in two 3-L Applikon glass bioreactors (Applikon Biotechnology, The Netherlands) using the same perfusion culture mode and same cultivation technology. The bioreactor controllers were marked as FC0A and FC0B for clarification. The bioprocess controller system used was Finesse G3Lab universal (Finesse Solutions, Inc., CA, USA).

The perfusion culture was operated using the ATF2 (Repligen, Pine Brook, NJ) cell retention system with 0.22 µm pore size, 1 mm inner diameter (ID) and 0.047 $m^2$ polyethersulfone filters. For basal medium feeding, the perfusion rate varied between 0.6 and 1.5 Volume/Volume/Day (VVD). And for feed medium, the perfusion rate varied between 0.2 and 0.4 VVD via semi-continuous dosing at an interval of 14.4 min. The cell bleeding was conducted through peristaltic pump manipulated by Finesse controller. Duration of the perfusion process was 38 days.

These two bioreactors were sampled twice per day for off-line analysis which were utilized as standard reference for modeling. Cell density, viability and cell diameter were measured using Vi-CELL (Vi-CELL XR, Beckman Coulter). pH, $pCO_2$, $pO_2$, $Na^+$ ions and $K^+$ ions were analyzed by Blood Gas Analyzer (Rapidlab BGA348EX, Siemens). Glucose, glutamine, glutamate, lactate, ammonium ions and titer were determined by Cedex (Cedex Bio HT, Roche). Osmolality was measured by Osmometer (Osmo PRO, Advanced Instruments, MA, USA).

2. Raman Spectral Acquisition

On-line Raman measurements were made by Kaiser RAMANRXN2 Multi-channel Raman Analyzer (Kaiser Optical Systems, Inc., Ann Arbor, MI) with a laser excitation wavelength of 785 nm. The base unit enables the use of a single-analyzer in support of up to 4 bIO-LAB-220 probes and can be used to monitor up to four bioreactors. Meanwhile, bIO-LAB-220 probes were immersed into our 3 L bench top bio-reactors. A typical laser power of 200 mW was also utilized. Each Raman spectrum was collected using a 10 s exposure time with 75 accumulations. Collection mode is continuous. Each spectrum took a total of about 13 mins to acquire. The analyzer was calibrated according to its manual before using and did auto-calibration once per day to ensure the wavelength accuracy during the cell culture.

3. Chemometric Modeling

The collected Raman spectrum was correlated to various standard reference measurements performed off-line with a software. The spectrum and reference pairs were exported in the format of csv files and then were analyzed and processed using Umetrics' SIMCA software version 14.1.2 (Umetrics Inc., San Jose, CA). Calibration spectra were first pre-processed by the Spectra Filter Module, and then correlated with the standard references via partial least square (PLS) regression.

Proper pre-processing of process spectral data is integral to create a well performing multivariate model. The pre-treatment usually used in our study is standard normal variate (SNV) followed by derivative. SNV processing was selected to reduce the effects of signal multiplying variations, arising from scattering by cells. Derivatives processing is useful in removing varying baselines. First or second derivative filter would be chosen for modeling for different parameters of interest based on the preprocessing performance. For this example, this kind of sequential pre-processing filtration obtained the best performance in the testing set. For spectra region selection, it is important to remove regions of the spectrum which consist primarily of noise, artifacts, Rayleigh scattering, or other non-Raman features. Generally modeling was restricted to the fingerprint region of the Raman spectra or selected according to the VIP index. After pre-processing and spectra region selection, independent PLS models were developed for glucose, lactate, ammonium ions and viable cell density (VCD) etc. Model results were evaluated through Observed vs. Predicted plot which displays the calculated $R^2$ and root mean square error of cross validation (RMSECV) and root mean square of prediction (RMSEP). Another important diagnostic tool the Hotelling's T2 could be used to understand the model hyper structure and detect outliers.

4. Integration of Raman into Bioprocess Controller

Raman RunTime system offers embedded OPC UA server. Finesse Trubio Delta V 5.0 was equipped with OPC function thus the predicted values could be obtained via the MatrikonOPC Data Manager (MatrikonOPC, Edmonton, Alberta, Canada). The integration and feedback control loop is shown in FIG. 1.

As shown in FIG. 1, two logic loops were existed for our control strategy. The first one is called process control loop in which the Raman signal is obtained in the 3-L bioreactor at a constant frequency, then it is transferred into a host computer, i.e., Runtime system, the SimcaKaiser module in the host computer could read the spectra file and turn it into the predicted values, then these values are communicated to the MatrikonOPC Data Manager through the local network, eventually Finesse TruBio DeltaV system reads these values and starts the pre-defined VCD auto-bleeding logic, this logic loop fulfills the VCD in-line auto-control. The second one is the modelling loop which has to be started once a new model needs to be built up.

5. Predictions of Key Biochemical Values for Perfusion Cell Culture

To test the possibility of utilizing Raman spectroscopy as a method to monitor the key biochemical values, i.e. IgG concentration, cell viability, glutamine concentration, glutamate concentration, glucose concentration, lactate concentration, $NH_4^+$ concentration, osmolality, $Na^+$ ions concentration, $K^+$ ions concentration, partial pressure of $CO_2$ ($pCO_2$) for perfusion cell culture, various PLS models were built up based on the data from FC0A. And their performance on the testing sets (FC0B) were shown in FIG. 4.

TABLE 1

Root mean square error of prediction (RMSEP) for testing sets

| Prediction Target | RMSEP |
|---|---|
| IgG (mg/L) | 147.48 |
| Viability (%) | 39 |
| Glutamine (mM) | 1.09 |
| Glutamate (mM) | 0.43 |
| Glucose (g/L) | 0.71 |
| Lactate (g/L) | 0.24 |
| $NH_4^+$ (mM) | 1.25 |
| Osmolality (mOsmo/kg) | 4.73 |
| $Na^+$ (mM) | 2.17 |
| $K^+$ (mM) | 0.67 |
| $pCO_2$ (mmHg) | 6.35 |

Figure 4:
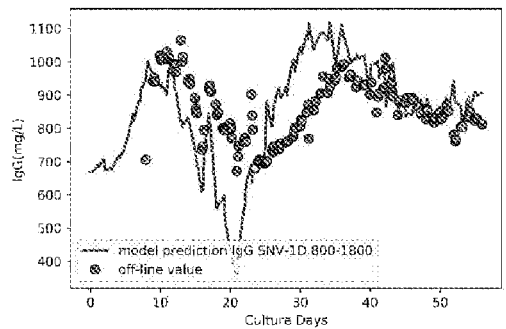
FIGS. 4(a)-(k) show prediction on target off-line biochemical indicators for testing sets (Model trained on FC0A data, Tested on FC0B data). Generally, both SNV-1D and SNV-2D are Raman signal preprocessing methods, either of which includes standard normal variate (SNV) and $1^{st}$ deriavtive or $2^{nd}$ deriavate consequently. Numeric range, i.e. 800-1800, represents the selected Raman shift range for modeling, VIP>0.5 indicates that the Raman shift range is selected where variable importance for the projection indicator (VIP) is larger than 0.5. (a) IgG SNV-1D 800-1800; (b) Viability SNV-1D VIP>0.5; (c) Glutamine SNV-1D VIP>0.5; (d) Viability SNV-1D VIP>0.5; (e) Glucose SNV-2D 800-1800; (f) Lactate SNV-1D 600-1700 VIP>0.5; (g) $NH_4^+$ SNV-1D 800-1600; (h) Osmolality SNV-1D 800-1800; (i) $Na^+$ SNV-1D 800-3400; (j) $K^+$ SNV-2D all wavelength; and (k) $pCO_2$ SNV-1D VIP>0.5.
Figure 4:
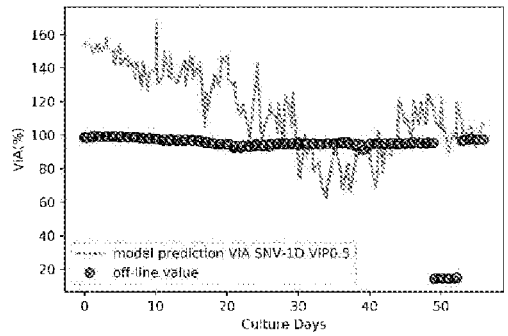
Figure 4:
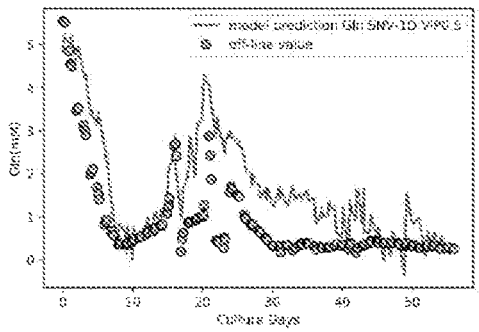
Figure 4:
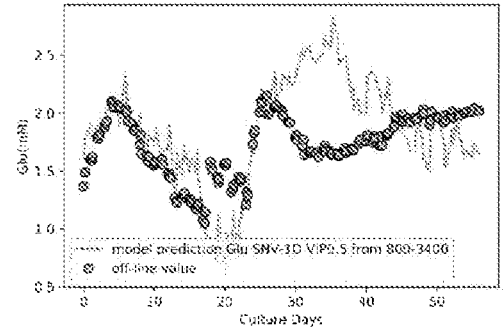
Figure 4:
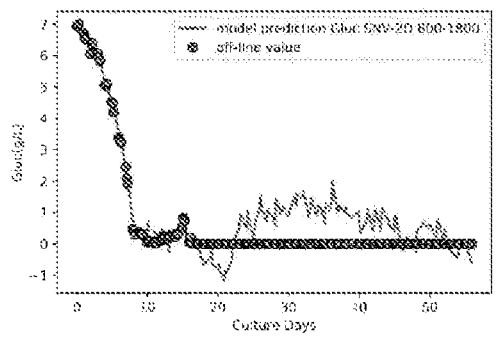
Figure 4:
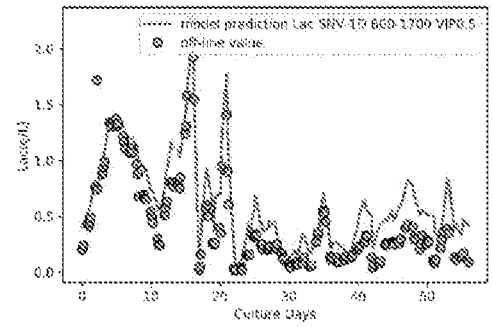
Figure 4:
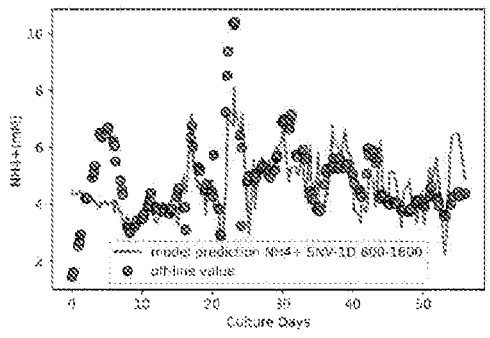
Figure 4:
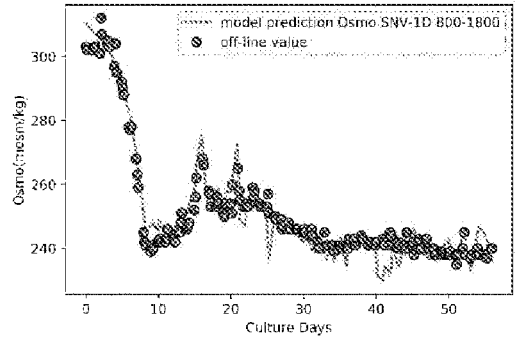
Figure 4:
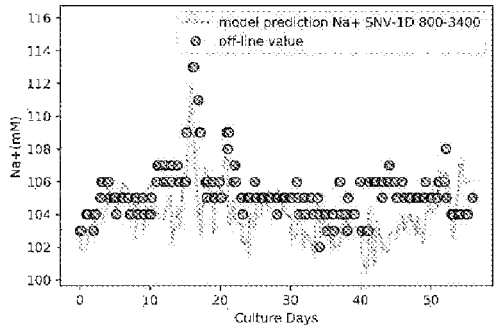
Figure 4:
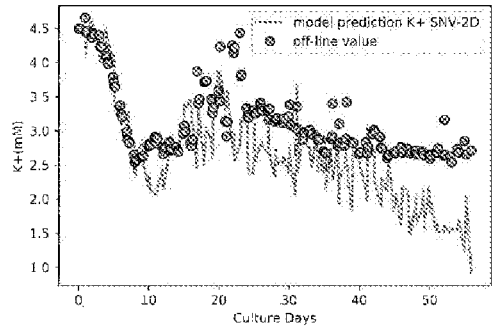
Figure 4:
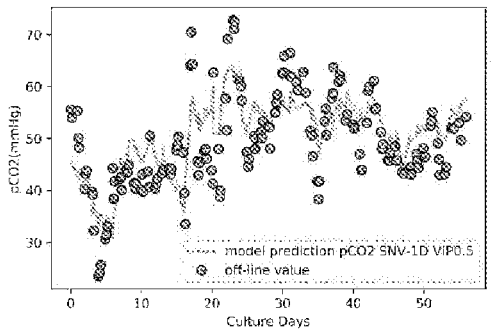

As shown in FIG. 4 and Table 1, the PLS model for IgG had acceptable predictions with a RMSEP of 147.48 mg/L, the error could be mainly attributed to the fluctuation of the predicted IgG concentration. The prediction for cell viability was unsatisfied, RMSEP was 39%, suggesting that more future work would be needed to optimize the model because cell viability for perfusion was not only regulated by cell density, cell metabolism condition or external environment like medium, but also strongly correlated with the basal feeding rate and bleeding rate. Considering these PLS models were only calibrated in one batch and prediction were more challenging in perfusion technology, for solutes like glutamine, glutamate, glucose and lactate, the predicting performances on testing sets were acceptable and reasonable. It's worth nothing that the bias for prediction on glutamate from Day 26 to Day 45 was probably caused by under-fitting of the model and technology differences from batch to batch. Model gave precise predictions on glucose concentration from Day 1 to Day 19, but the performance became worse after Day 19 as the glucose in the bioreactor gradually decreased to zero which indicated a dynamic balance of glucose feeding, out and consumption. The fixed position of the probe in the bioreactor and the heterogeneity of the cultured medium might led to the increased prediction error for glucose concentration. Raman also gave us good results on ions such as $NH_4^+$, $Na^+$, $K^+$. The predicted $K^+$ ions concentration slightly drifted in the late phase of culture, which was caused by the accumulated differences between FC0A (training sets) and FC0B (testing sets) in the late phase of cell culture. Performance on osmolality was great with a RMSEP of 4.73 mOsmo/kg which meant the osmolality could be exactly predicted if same basal and feed medium were selected as the calibration batch in perfusion cell culture. And also, the Raman spectroscopy also showed potential to predict the partial pressure of carbon dioxide in the bioreactor for perfusion.

6. Conclusion

The present disclosure established the state-of-the-art perfusion cell culture-Raman integrated system where key parameters on-line monitoring and viable cell density in-line auto-control were both archived. It was shown that most key parameters, i.e. glucose, lactate, osmolality and IgG concentration could be predicted precisely with RMSEP of 0.71 g/L, 0.24 g/L, 4.73 mOsmo/kg and 147.48 mg/L respectively using the model with calibration data from just one batch, and some parameters, i.e. glutamate, glutamine, partial pressure of $CO_2$, $Na^+$ ions concentration and $K^+$ ion concentration could also be predicted with acceptable accuracy. The work established solid foundations for PAT implementation in biologics continuous manufacturing, showed great potentials for regulating product quality in-line, offered a robust tool to address the quality issues for biologics continuous manufacturing.

Example 2

1. Auto Feedback Control of Perfusion VCD Bleeding

The bioreactor VCD was maintained at $50 \times 10^6$ cells/mL of the set-point by means of ±2 deadband control. When the online VCD increased above the upper deadband, the controller peristaltic pump was initiated to bleed cell out. The pump speed was determined by PID (proportional-integral-derivative) control and output scaling. The pump worked at a constant speed until next online VCD was measured. If the new generated VCD was still above the upper deadband, the pump continued to work but at a new calculated speed. If not, the pump would stop.

2. Raman Spectra for Perfusion Cell Culture

Figure 3:
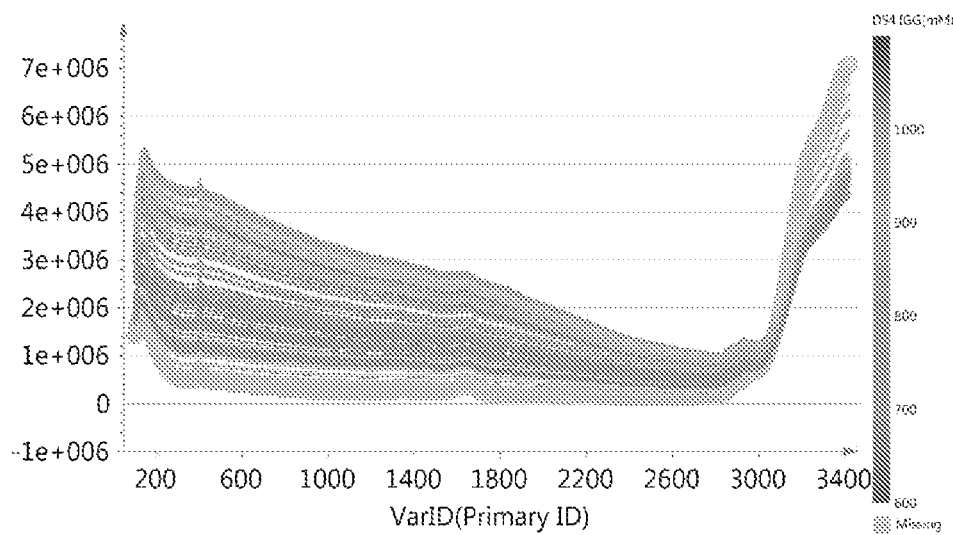
FIG. 3 shows Raman spectra raw data for one perfusion experiment (FC0B).

The Raman spectra raw data for one perfusion experiment was shown in FIG. 3, where the y-axis represents the Raman intensity, x-axis represents the Raman shift from 100 $cm^{-1}$ to 3400 $cm^{-1}$. Each line in this figure represents one Raman curve at that moment where the color indicates the measured IgG concentration.

3. Modeling for Viable Cell Density

To implement auto-control of VCD, it's extremely important to obtain a robust, accurate PLS model for VCD prediction. An accurate prediction of VCD in-real time could help the controller to make quick and correct response in the process in-line control loop. Thus, 6 different models with different Raman signal preprocessing methods and data sources were compared, i.e. two derivative and 3 data sources.

Data source variation could bring considerable effects to the model calibration space and lead to distinct model performance for VCD prediction. Considering auto-control was planning in bioreactor FC0A, so the first data source we considered for VCD modeling was the Raman data from historical data in FC0A, which means predicting VCD for FC0A from Day 51 based on its historical data from Day 1 to Day 50. Second data source was from the paralleled bioreactor FC0B. The third data source for training the model was the cultured data from both FC0B and FC0A (Day 1-50).

Figure 5:
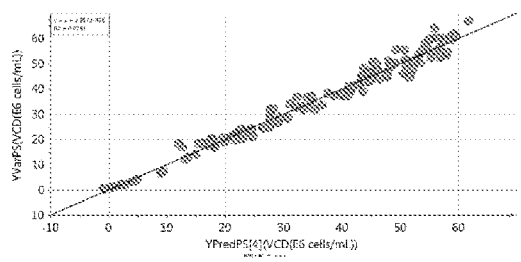
FIGS. 5(a)-(f) show predictions on VCD for training sets based on different models. (a) Preprocessing method SNV and $1^{st}$-Derivative, data source: bioreactor FC0A from Day 1 to Day 50, (b) Preprocessing method SNV and $2^{nd}$-Derivative, data source: bioreactor FC0A from Day 1 to Day 50, (c) Preprocessing method SNV and $1^{st}$-Derivative, data source: bioreactor FC0B, (d) Preprocessing method SNV and $2^{nd}$-Derivative, data source: bioreactor FC0B, (e) Preprocessing method SNV and $1^{st}$-Derivative, data source: bioreactor FC0A from Day 1 to Day 50 and FC0B, and (f) Preprocessing method SNV and $2^{nd}$-Derivative, data source: bioreactor FC0A from Day 1 to Day 50 and FC0B.
Figure 5:
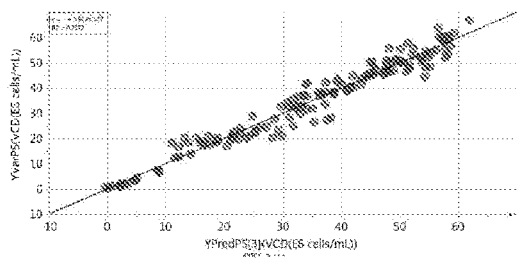
Figure 5:
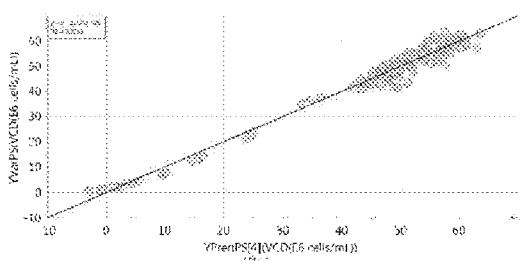
Figure 5:
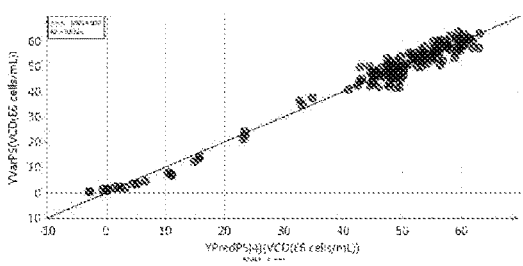
Figure 5:
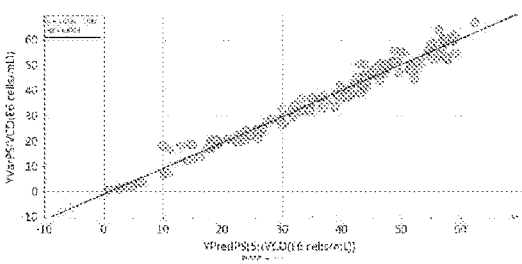
Figure 5:
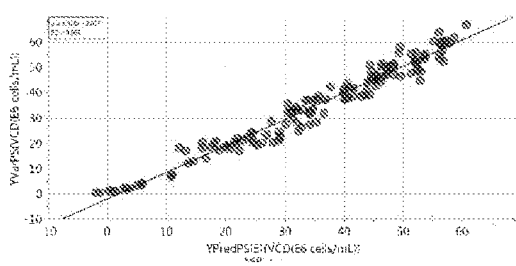

As shown in FIG. 5, all 6 PLS models had acceptable preditive performance on training set, especially for the model based on $1^{st}$ derivative of Raman spectra (left hand side). And also, data points were loacated in different ranges for models with different data sources. More detailly, training data from FC0A, day 1-50 had more even VCD data distribution, however training data from FC0B had higher possibility to locate at the range VCD from 45 to $60 \times 10^6$ cells/ml.

Figure 6:
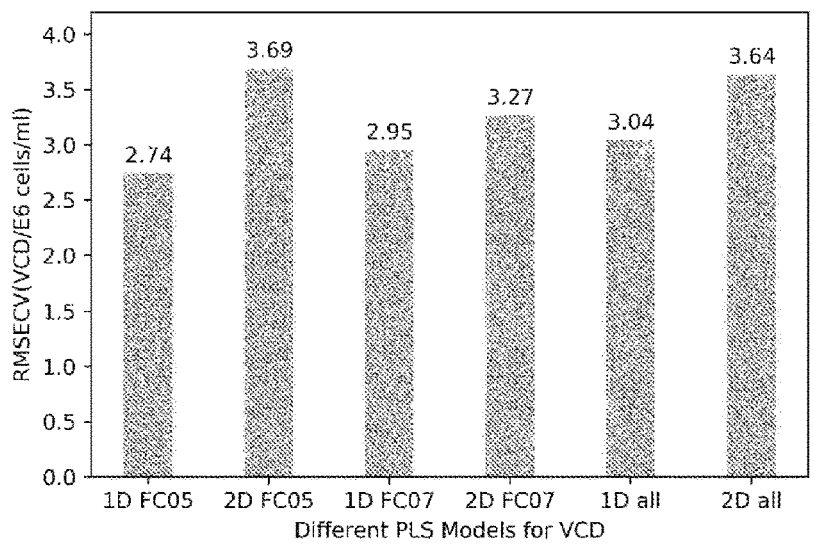
FIG. 6 shows root mean squre error on different PLS models for VCD for training sets.
Figure 7:
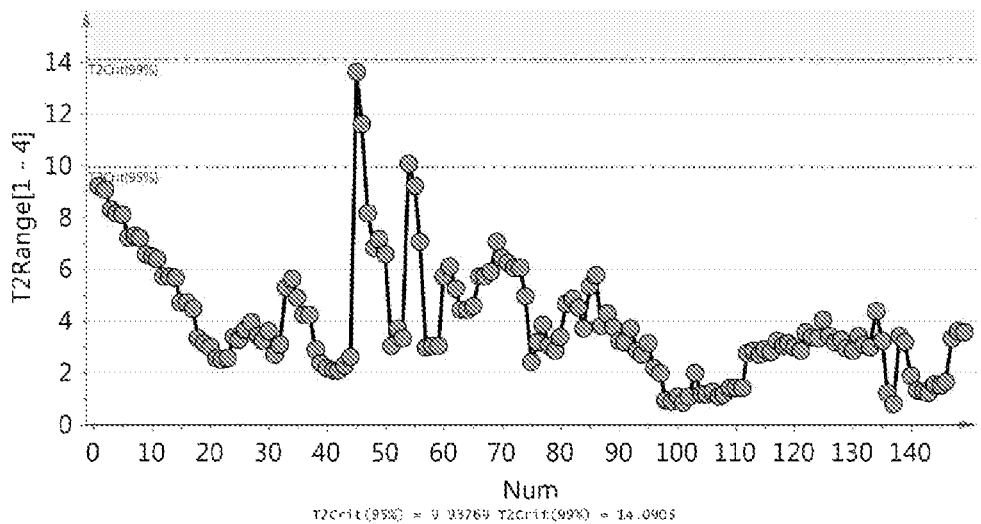
FIGS. 7(A)-(B) show Hotelling's T2-range for two different Raman data preprocessing methods: (A) $1^{st}$ derivative, (B) $2^{nd}$ derivative (Data source: FC0A 1-50 days).
Figure 7:
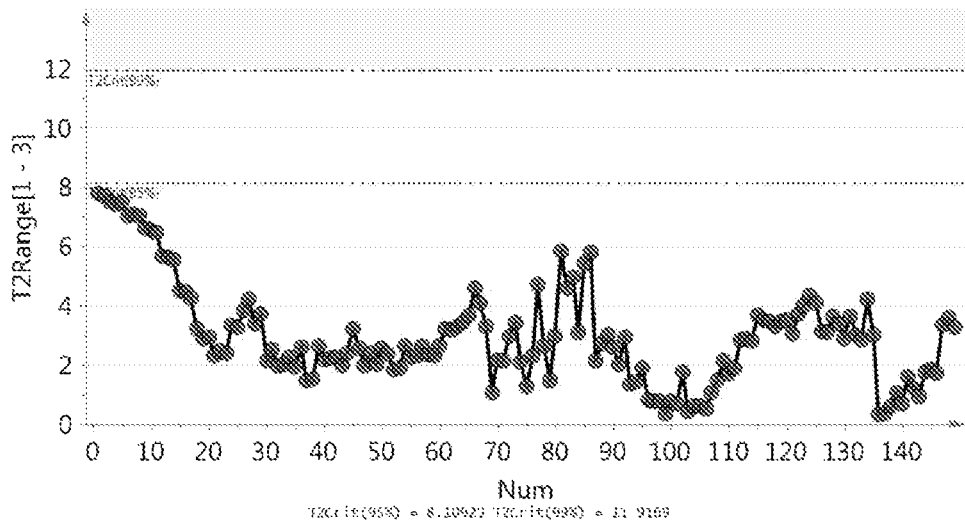

As shown in FIG. 6, generally, the RMSECV (Root Mean Square Error of Cross Validation) on training sets of $1^{st}$ derivative was lower than the RMSE of $2^{nd}$ derivative, but lower training RMSE could bring more risks on over-fitting based on our experience.

Furthermore, two kinds of derivative methods were compared in the aspects of Hotelling's T2-range value. As shown in FIG. 6 (a), for model built up by $1^{st}$ derivative, some points were above the 95% confidence limit, indicating that the model quality would be effected by the $1^{st}$ derivative preprocessing. Therefore, the results suggested $2^{nd}$ derivative preprocessing was better than $1^{st}$ derivative from the point of view of Hotelling's T2-range chart.

Figure 8:
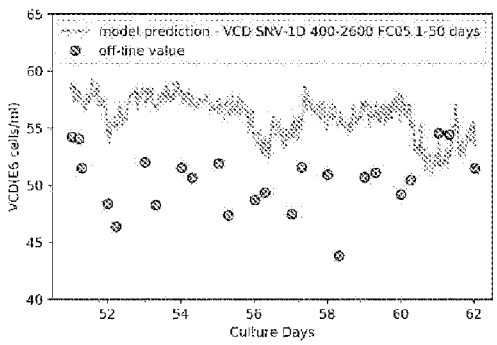
FIGS. 8(a)-(f) show predictions on VCD for testing sets (FC0A Day51-Day62) and the subtitle for each sub-figure indicates the modeling method and calibration dataset. (a) SNV-1D FC0A 1-50 days; (b) SNV-2D FC0A 1-50 days; (c) SNV-1D FC0B; (d) SNV-2D FC0B; (e) SNV-1D FC0A 1-50 days and FC0B; and (f) SNV-2D FC0A 1-50 days and FC0B.
Figure 8:
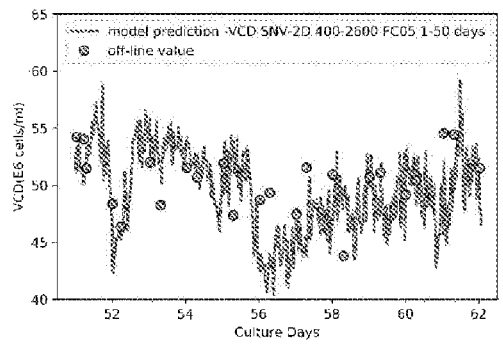
Figure 8:
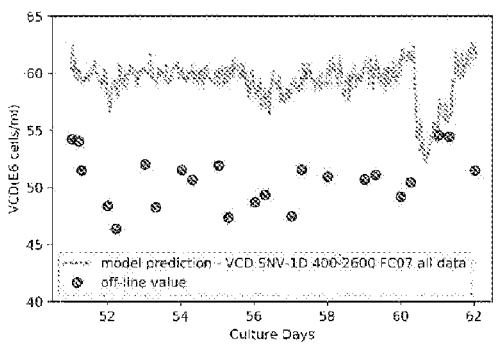
Figure 8:
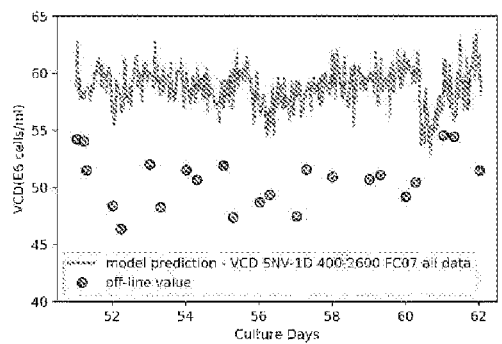
Figure 8:
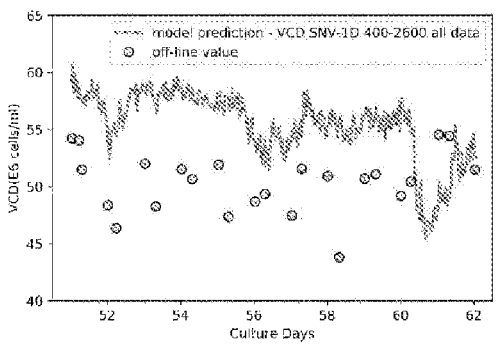
Figure 8:
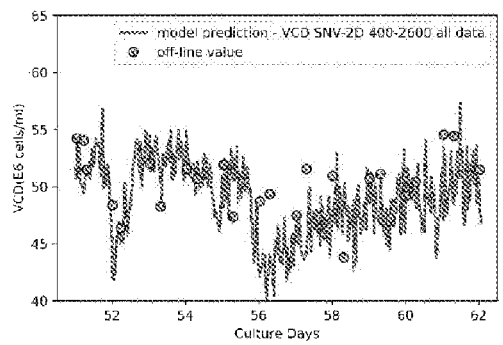
Figure 9:
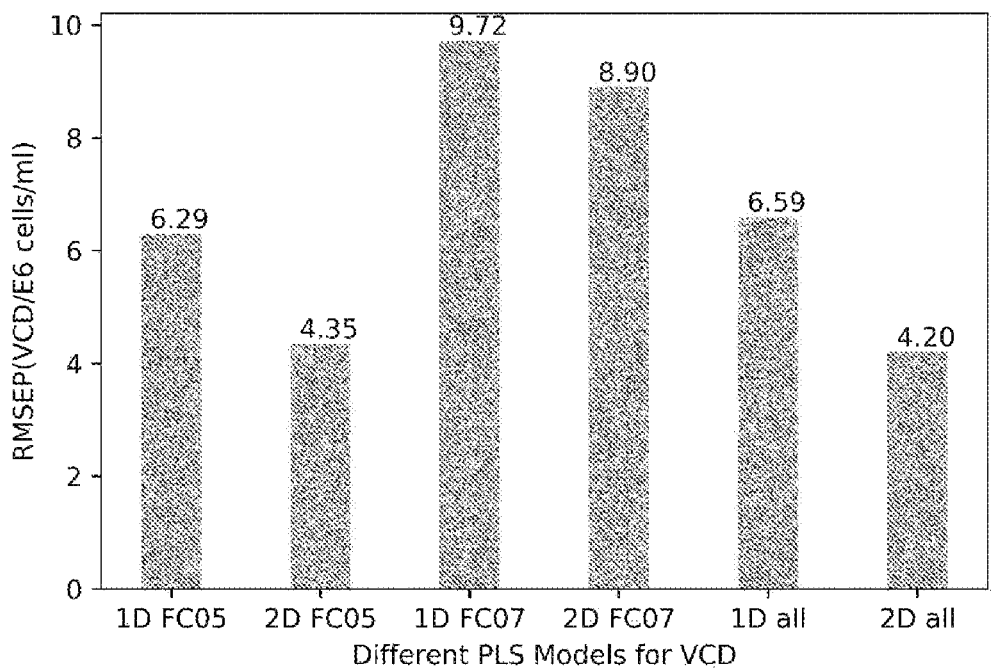
FIG. 9 shows root mean square error of prediction (RMSEP) for different VCD models.

The results for the testing performance on VCD based on different models are shown in FIGS. 8 and 9. Those PLS models for VCD predictions had different testing performances due to different data preprocessing methods and data sources. It's worth nothing that PLS models with $2^{nd}$ derivative preprocessing on Raman spectra all had lower RMS error of prediction than $1^{st}$ derivative. Consistently, the predicted VCDs using $1^{st}$ derivative were all overestimated, which illustrated that in our case $1^{st}$ derivative on Raman spectra would introduce bias for modeling. Furthermore, $2^{nd}$ derivative removed this bias, but the variance increased as indicated by the fluctuation of predicted VCD.

In addition, data source also had some influences on the VCD prediction performance. In detail, historical data was much better than the data from another batch (FC0B), which were reasonable considering the difference from batch to batch in perfusion. Besides, the results from FIG. 9 also indicated putting the data from FC0B into training dataset made by FC0A did not improve the performance.

4. Conclusion

Results also showed that $2^{nd}$ derivative preprocessing on the Raman spectra had better performance in the VCD prediction than $1^{st}$ derivative, and historical data from the batch itself was better than the paralleled batch for VCD modelling and calibration.

Example 3

1. Auto-Control for VCD in Small Scale (1500 mL in 3 L Bioreactor)

As mentioned before, the $2^{nd}$ derivative model with the data from FC0A or $2^{nd}$ derivative model with the data trained with data from FC0A and F07 had matched prediction capacity. So $2^{nd}$ derivative model with the data from FC0A was selected where we assumed historical data from itself would not introduce extra bias for the VCD model.

Here, as shown in FIG. 2, the diagram showed how we implemented auto-bleeding in our perfusion system. Firstly, perfusion was archived as feed medium was continuously feed into the bioreactor, product was continuously harvested with the help of cell retention system. Before the automatically control of VCD, cells were bled out of the bioreactor at a constant pumping rate which needs to be modified periodically. While Raman spectroscopy could detect the scattered laser intensity in the reactor and transfer the signal into multivariate values, those predicted biochemical indices were then delivered to the deltaV controller through OPC connection. In the deltaV controller, the difference between the real-time VCD and VCD set-point was put into the P.I.D (proportional-integral-derivative) algorithms, then the output, i.e. controller output went through the configuration setting, were scaled to the suitable actuator output, eventually a pump was cascaded to the actuator output. Namely, the power of the pump was set to be proportional to the difference between the predicted VCD and target VCD. Besides, a high limit for pump power was set to ensure the system safety. P.I.D. strategy was also utilized to smooth and stabilize the on-line control of VCD.

TABLE 2

Summary of VCD auto-control in 3 L Bench Bioreactor

|  | Average Value ($\times 10^6$ cells/ml) | Standard Deviation ($\times 10^6$ cells/ml) |
| --- | --- | --- |
| Target VCD | 50.0 | — |
| Predicted VCD | 50.98 | 1.76 |
| Off-line VCD | 50.67 | 2.67 |

Figure 10:
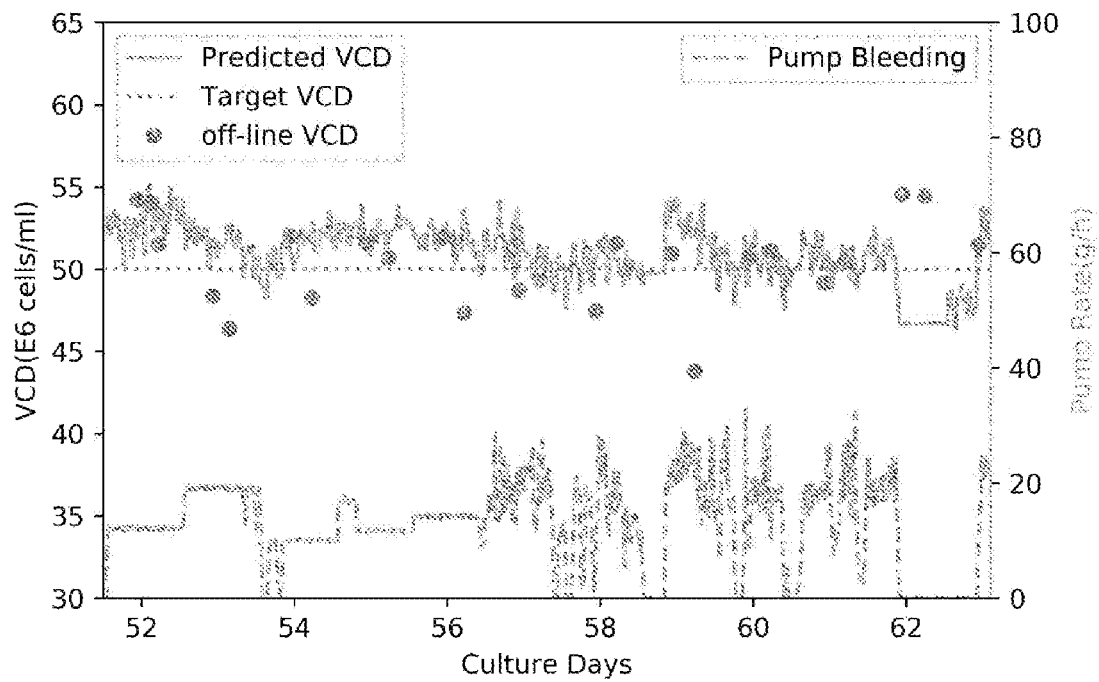
FIG. 10 shows auto-controlled VCD and corresponding pump rate in FC0A as a function of culture days.

The results for auto-control of VCD was displayed in FIG. 10. It's shown in FIG. 10 that a target VCD was set to $50 \times 10^6$ cells/ml, which was a recommended setting for perfusion cell culture. Compared to the red filled circle, predicted VCD values indicated by cyan line were acceptable. And also, the predicted values fluctuated around target VCD, i.e. $50 \times 10^6$ cells/ml. Once the on-line predicted VCD was higher than $50 \times 10^6$ cells/ml, the pump would start to work as described above. And the pump rate would gradually decrease to 0 with the help of P.I.D control strategy once the updating VCD could decrease to the target VCD. As shown in FIG. 10, it was obvious that off-line VCD had higher amplitude around target VCD, suggesting more optimization were needed for the future work.

Results in Table 2 also showed that the standard deviation of controlled VCD from Day 51 to Day 62 were 1.76 and 2.67, for on-line and off-line values respectively, which was consistent with the trends in FIG. 10. The average value for both predicted on-line VCD and off-line VCD were greatly maintained at the target VCD, i.e. 50.98 and 50.67 respectively. So those results demonstrated a feasible auto-control strategy for VCD in perfusion of mammalian cell culture was developed successfully.

2. Conclusion

A feasible auto-control strategy for VCD in perfusion mammalian cell culture was developed where the on-line and off-line VCD were maintained around the target VCD of $50 \times 10^6$ cells/ml, i.e. $50.98 \pm 1.76$ and $50.67 \pm 2.67$ respectively for 11 days.

Example 4

1. Auto-Control for VCD in Large Scale (60 L in 200 L Bioreactor)

Benefited from the scalability and specificity of Raman spectrum, the model built in small scale, i.e., 3 L could directly be utilized in large scale (e.g., 60 L, for example, in 200 L XDR bioreactor) for VCD on-line monitoring and feedback control. The cultivation in perfusion mode using a 200 L XDR bioreactor with a constant working volume of ~60.0 L for scale-up validation. And to ensure the robustness of the auto-control process during the scaling-up, once the difference between on-line and off-line measured VCD is larger than $5 \times 10^6$ cells/ml, the latest data from larger scale would be added into the dataset of the PLS model for VCD to improve the cross-scale model accuracy.

Figure 11:
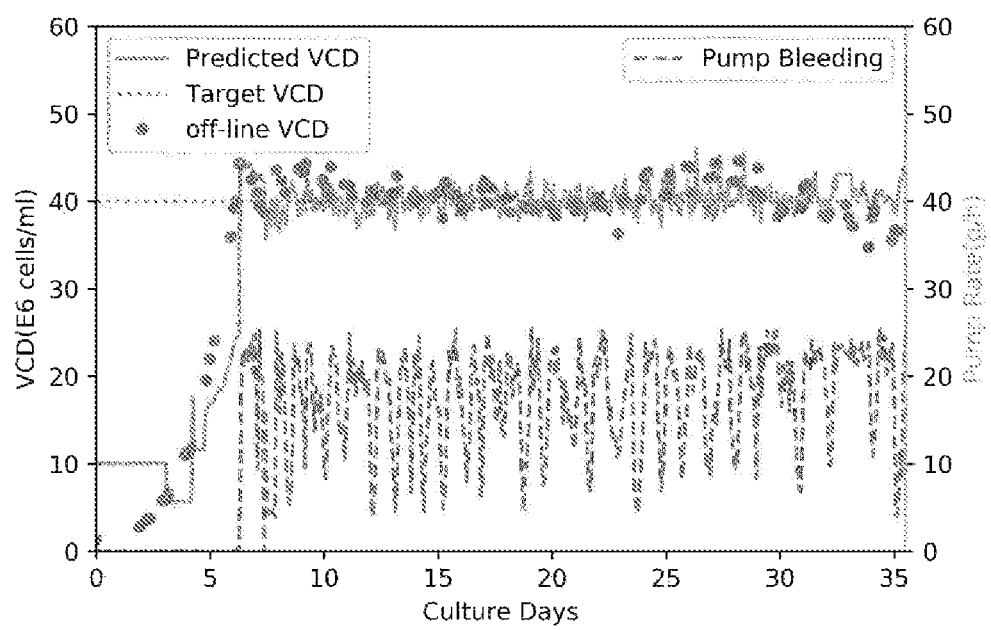
FIG. 11 shows auto-controlled VCD and corresponding pump rate in large scale culture (60 L) as a function of culture days.

The results for auto-control of VCD in 200 L XDR bioreactor was displayed in FIG. 11. It's shown in FIG. 11 that a target VCD was set to $40 \times 10^6$ cells/ml, which was a recommended setting for perfusion cell culture. Compared to the filled circle, predicted VCD values as indicated were acceptable. Also, the predicted values fluctuated around target VCD, i.e. $40 \times 10^6$ cells/ml. Once the on-line predicted VCD was higher than $40 \times 10^6$ cells/ml, the pump would gradually start to work as described above. And the pump rate would gradually decrease to 0 with the help of P.I.D control strategy once the updating VCD could decrease to the target VCD. As shown in FIG. 11, it was obvious that on-line VCD was relatively accurate and it was well controlled around target VCD. With the help of Raman Analyzer and the model built in small scale as well as the P.I.D control strategy, a steady perfusion state with a target VCD of $40 \times 10^6$ cells/ml was maintained for more than 28 days (after Day 7).

TABLE 3

Summary of VCD auto-control in 60 L Perfusion Run

|  | Average Value ($\times 10^6$ cells/ml) | Standard Deviation ($\times 10^6$ cells/ml) |
| --- | --- | --- |
| Target VCD | 40.0 | — |
| Predicted VCD | 40.30 | 1.33 |
| Off-line VCD | 40.69 | 1.96 |

As shown in Table 3, for scale-up in 60 L, the standard deviation of controlled VCD (calculated when auto-control start) from Day 6 to Day 35 were 1.33 and 1.96, for on-line and off-line values respectively. The average value for both predicted on-line VCD and off-line VCD were greatly maintained at the target VCD, i.e. 40.69 and 40.30 respectively, indicating a more stable and accurate VCD control was archived in large scale.

2. Conclusion

This successful scale up in 60 L indicated the feasibility and scalability of Raman analyzer. Also, a more accurate and stable VCD profiles were obtained in large scale because of the data accumulation and accordingly improved model robustness and accuracy, showing the strong potential of Raman to control VCD in the perfusion mammalian cell culture process.

Those skilled in the art will further appreciate that the present invention may be embodied in other specific forms without departing from the spirit or central attributes thereof. In that the foregoing description of the present invention discloses only exemplary embodiments thereof, it is to be understood that other variations are contemplated as being within the scope of the present invention. Accordingly, the present invention is not limited to the particular embodiments that have been described in detail herein. Rather, reference should be made to the appended claims as indicative of the scope and content of the invention.

REFERENCES

[1]. U.S. Food and Drug Administration. Guidance for industry, PAT-A Framework for Innovative Pharmaceutical Development, Manufacturing and Quality Assurance. http://www.fda.gov/cder/guidance/published.html (2004).

[2]. Molony, Michael, and Cenk Undey. "PAT tools for biologics: considerations and challenges." Quality by Design for Biopharmaceuticals: Principles and Case Studies (2009): 211-253.

[3]. Gagnon, Matthew, et al. "Shift to high-intensity, low-volume perfusion cell culture enabling a continuous, integrated bioprocess." Biotechnology progress 34.6 (2018): 1472-1481.
[4]. U.S. Food and Drug Administration. Quality consideration for continuous manufacturing guidance for industry. http://www.fda.gov/cder/guidance (2019).
[5]. Gronemeyer, Petra, Reinhard Ditz, and Jochen Strube. "Trends in upstream and downstream process development for antibody manufacturing." Bioengineering 1.4 (2014): 188-212.
[6]. Riley, Mark R., Carl D. Okeson, and Brenna L. Frazier. "Rapid calibration of near-infrared spectroscopic measurements of mammalian cell cultivations." Biotechnology progress 15.6 (1999): 1133-1141.
[7]. Kozma, Bence, et al. "On-line prediction of the glucose concentration of CHO cell cultivations by NIR and Raman spectroscopy: Comparative scalability test with a shake flask model system." Journal of pharmaceutical and biomedical analysis 145 (2017): 346-355.
[8]. Mehdizadeh, Hamidreza, et al. "Generic Raman-based calibration models enabling real time monitoring of cell culture bioreactors." Biotechnology progress 31.4 (2015): 1004-1013.

The invention claimed is:

1. A Raman spectroscopy integrated perfusion cell culture system for monitoring and auto-controlling perfusion cell culture, comprising:
   a bioreactor, comprising:
   (1) an interior chamber for receiving a cell culture,
   (2) a port for feeding nutrient materials from a feed reservoir into the interior chamber,
   (3) a port for auto-bleeding from the interior chamber, and
   (4) a port for continuously harvesting materials from the interior chamber with the help of a cell retention system;
   a Raman analyzer, comprising (i) one or more Raman probes which are immersed into the bioreactor and are configured to collect Raman spectrum in the bioreactor, and (ii) a host computer which is configured to receive the Raman spectrum collected and transferred by the Raman probe(s) and turn it into biochemical parameter values; and
   a controller in communication with the Raman analyzer, the feed reservoir and an auto-bleeding device, the controller being configured to receive the values from the Raman analyzer and compare them with preset parameters, and the controller further being configured to control the feed reservoir for adjusting the feeding rate of nutrient materials into the bioreactor, and being configured to control the auto-bleeding device for auto-bleeding materials from the bioreactor, based on results from comparing action.

2. The Raman spectroscopy integrated perfusion cell culture system according to claim 1, wherein the cell retention system is coupled to the bioreactor via the port for continuously harvesting materials from the interior chamber.

3. The Raman spectroscopy integrated perfusion cell culture system according to claim 1, wherein the cell retention system is selected from an Alternating Tangential Filtration (ATF) system, a Tangential Flow Filtration (TFF) system, an internal microfiltration system, a dielectrophoresis system, an acoustic resonance system or a gravitation, sedimentation system.

4. The Raman spectroscopy integrated perfusion cell culture system according to claim 1, wherein the system further comprises a product harvest reservoir.

5. The Raman spectroscopy integrated perfusion cell culture system according to claim 1, wherein the bioreactor further comprises a rotatable shaft coupled to an agitator.

6. The Raman spectroscopy integrated perfusion cell culture system according to claim 1, wherein the Raman analyzer comprises two or more Raman probes, which measure different signals relative to each other.

7. The Raman spectroscopy integrated perfusion cell culture system according to claim 1, wherein the Raman probes are configured to collect Raman spectrum in the bioreactor by detecting an intensity of scattered light in the bioreactor after the cell culture is exposed to a beam of light periodically.

8. The Raman spectroscopy integrated perfusion cell culture system according to claim 7, wherein the Raman analyzer further comprises a laser-emitting module which emits a laser into the bioreactor with excitation wavelength of 785 nm periodically.

9. The Raman spectroscopy integrated perfusion cell culture system according to claim 1, wherein the system further comprises a cover made of light-impermeable material, and the cover is configured to cover the bioreactor when the laser-emitting module of the Raman analyzer emits a laser into the bioreactor periodically and the Raman probes collect the Raman spectrum by detecting an intensity of scattered light in the bioreactor.

10. The Raman spectroscopy integrated perfusion cell culture system according to claim 9, wherein the system is configured to incubate mammalian cells.

11. The Raman spectroscopy integrated perfusion cell culture system according to claim 1, wherein the collected Raman spectrum is correlated to biochemical indices selected from viable cell density (VCD), cell diameter, pH, $pCO_2$, $pO_2$, $Na^+$ ions and $K^+$ ions, glucose, glutamine, glutamate, lactate, ammonium ions and titer, or osmolality.

12. The Raman spectroscopy integrated perfusion cell culture system according to claim 1, wherein the system is configured to incubate animal cells, plant cells, bacteria cells or fungi cells.

13. A process for monitoring and auto-controlling perfusion cell culture by using the Raman spectroscopy integrated perfusion cell culture system according to claim 1, comprising:
   (a) culturing a starting amount of cells in a starting volume of basal medium in a bioreactor,
   (b) collecting Raman spectrum by one or more Raman probes after exposing the cell culture to a beam of light periodically, and converting the collected Raman spectrum to biochemical indices by a host computer; and
   (c) adjusting feeding rate of nutrient materials from a feed reservoir into the bioreactor and auto-bleeding rate of the materials from the bioreactor by a controller based on results from comparing the biochemical indices with corresponding preset parameter values input into the controller.

14. The process according to claim 13, further comprising continuously harvesting a cell product of interest from the bioreactor with the help of a cell retention system, and/or maintaining cells in the bioreactor based on their sizes through a cell retention system.

15. The process according to claim 14, wherein the cell retention system is selected from an Alternating Tangential Filtration (ATF) system, a Tangential Flow Filtration (TFF)

system, an internal microfiltration system, a dielectrophoresis system, an acoustic resonance system or a gravitation, sedimentation system.

16. The process according to claim 13, wherein the collected Raman spectrum is correlated to biochemical indices selected from viable cell density (VCD), cell diameter, pH, $pCO_2$, $pO_2$, $Na^+$ ions and $K^+$ ions, glucose, glutamine, glutamate, lactate, ammonium ions and titer, and osmolality.

17. The process according to claim 13, wherein the process is used to continuously incubate animal cells, plant cells, bacterial cells, or fungi cells.

18. The process according to claim 17, wherein the process is used to continuously incubate mammalian cells.

19. The process according to claim 18, wherein the process is used to continuously incubate Chinese hamster ovary (CHO) cells, hybridomas, Baby Hamster Kidney (BHK) cells, myeloma cells, HEK-293 cells, human lymphoblastoid cells, E1 immortalized HER cells, NSO cells or SP/20 cells.

20. The process according to claim 13, wherein the cells produce products of interest.

* * * * *